US009084788B2

(12) United States Patent
Ford

(10) Patent No.: US 9,084,788 B2
(45) Date of Patent: *Jul. 21, 2015

(54) COMPOSITIONS AND METHODS FOR TREATING AND PREVENTING DERMATOSES

(75) Inventor: John P. Ford, Unadilla, NY (US)

(73) Assignee: Asymmetric Therapeutics, LLC, Unadilla, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/566,632

(22) Filed: Aug. 3, 2012

(65) Prior Publication Data
US 2012/0295929 A1 Nov. 22, 2012

Related U.S. Application Data

(63) Continuation of application No. 12/893,692, filed on Sep. 29, 2010, now Pat. No. 8,258,147, which is a continuation of application No. 12/114,602, filed on May 2, 2008, now Pat. No. 7,816,366, which is a continuation of application No. 12/073,424, filed on Mar. 5, 2008, now Pat. No. 7,662,829, which is a continuation of application No. 11/196,921, filed on Aug. 3, 2005, now Pat. No. 7,368,456, which is a continuation of application No. 10/918,199, filed on Aug. 13, 2004, now Pat. No. 6,995,165, which is a continuation-in-part of application No. 10/684,203, filed on Oct. 10, 2003, now Pat. No. 6,979,688, which is a continuation-in-part of application No. 10/364,383, filed on Feb. 12, 2003, now abandoned.

(60) Provisional application No. 60/355,764, filed on Feb. 12, 2002.

(51) Int. Cl.
A01N 43/54 (2006.01)
A61K 31/505 (2006.01)
A61K 31/513 (2006.01)
A61K 31/00 (2006.01)
A61K 31/337 (2006.01)
A61K 31/555 (2006.01)
A61K 31/704 (2006.01)
A61K 31/7072 (2006.01)

(52) U.S. Cl.
CPC ............. A61K 31/513 (2013.01); A61K 31/00 (2013.01); A61K 31/337 (2013.01); A61K 31/505 (2013.01); A61K 31/555 (2013.01); A61K 31/704 (2013.01); A61K 31/7072 (2013.01)

(58) Field of Classification Search
CPC ... A61K 31/00; A61K 31/337; A61K 31/505; A61K 31/513; A61K 31/555; A61K 31/704; A61K 31/7072; A61K 2300/00
See application file for complete search history.

(56) References Cited

U.S. PATENT DOCUMENTS

| 6,979,688 | B2* | 12/2005 | Ford | 514/274 |
| 6,995,165 | B2* | 2/2006 | Ford | 514/274 |
| 7,368,456 | B2* | 5/2008 | Ford | 514/274 |
| 7,662,829 | B2* | 2/2010 | Ford | 514/274 |
| 7,816,366 | B2* | 10/2010 | Ford | 514/274 |
| 8,258,147 | B2* | 9/2012 | Ford | 514/274 |
| 2003/0158128 | A1 | 8/2003 | Ford | |

OTHER PUBLICATIONS

Barrows, parts of "Antineoplastic and Immunoactive Drugs," Chapter 86 in Remington: The Science and Practice of Pharmacy, 20th Edition, Gennaro et al. (eds.), Lippincott, Williams & Wilkins, Baltimore, MD, 2000, only pp. 1498 and 1815 supplied.*
Sigma U.S. Catalog, "Biochemical and Reagents for Life Science Research," St. Louis, MO, 2000-2001 edition, only p. 1000 supplied.*
(T) Swinyard et al., "Pharmaceutical Necessities," Chapter 66 in Remington's Pharmaceutical Sciences, 18th Edition, Gennaro et al (eds.), Mack Publishing Co., Easton, PA, 1990, only pp. 1286-1329 supplied.*
(U) Nairn, J. G., "Solutions, Emulsions, Suspensions and Extracts," Chapter 83 in Remington's Pharmaceutical Sciences, 18th Edition, Gennaro et al.(eds.), Mack Publishing Co., Easton, PA, 1990, only pp. 1519-1544 supplied.*
(V) Weast et al., CRC Handbook of Chemistry and Physics, Boca Raton, FL, 1981, only p. C-536 supplied: see entry for "Uracil."*
(W) Beers et al. (eds.), Chapter 126 ("Malignant Tumors") in The Merck Manual of Diagnosis and Therapy, 17th Edition, Merck & Co., Inc., Rahway, NJ, Jan. 1999, only title pages and text pp. 842-843 supplied.*
(X) Venes et al.(eds.), Taber's Cyclopedic Medical Dictionary, 21st Edition, F. A. Davis Co., Philadelphia, PA, 2009, see pp. 285-289 ("carcinoma").*
Pugh et al. (eds.), Stedman's Medical Dictionary, 27th Edition, Lippincott Williams & Wilkins, Baltimore, MD, 2000, see pp. 365, 613-617 & 620 ("carcinoma," "dermatitis," "dermatosis & dermatoses").*
Childress, J. et al.: "Cutaneous Hand and Foot Toxicity Associated with Cancer Chemotherapy". American Journal of Clinical Oncology, vol. 26(5), pp. 435-436, 2003.
Chua, D., et al.: "Efficacy of Capecitabine Monotherapy in Patients with Recurrent and Metastatic Nasopharyngeal Carcinoma Pretreated with Platinum-Based Chemotherapy", Proc. Am Soc. Clin. Oncol. vol. 22, p. 511, 2003.
Ehrlanger, et al.: "Cutaneous Absorption and Urinary Excretion of 6-14C-5-5-Fluorouracil Ointment Applicated in an Ointment to Healthy and Diseased Human Skin", Dermatologica, vol. 140, Suppl. 1, pp. 129-136, 1970.

(Continued)

Primary Examiner — Lawrence E Crane
(74) Attorney, Agent, or Firm — Fanelli Haag PLLC

(57) ABSTRACT

The invention encompasses protectant agents including uracil or a metabolite thereof that effectively treat the cutaneous toxicities and dermatological side-effects associated with chemotherapeutic agents. Specifically, and surprisingly, the compositions of the invention including uracil or a metabolite thereof are effective for treating various dermatoses including atopic dermatitis, irritant contact dermatitis, radiation-induced dermatitis, dry skin dermatitis, papulopustular rashes, xerosis, pruritus, actinic keratosis, and genital warts.

9 Claims, 10 Drawing Sheets

(56) References Cited

OTHER PUBLICATIONS

Elasmer, et al.: "Case Report: Hand-Foot Syndrome Induced by Oral Fluoropyrimidine S-1", Jpn. J. Clin. Oncol., vol. 3(4), p. 172-174, 2001.
Findlay, M., et al.: "Measurement and Plasma 5-Fluorouracil by High-Performance Liquid Chromatography with Comparison of Results to Tissue Drug Levels Observed Using in Vivo 19F Magnetic Resonance Spectroscopy in Patients in Protracted Venous Infusion with or without Interferon-α", Annals of Oncology, vol. 7(47-53), pp. 111-117, 1996.
Fishcel, J. L., et al.: "Experimental Arguments for a better Understanding of Hand-Foot Syndrome Under Capacitabine", Proceedings of the American Association for Cancer Research, vol. 45, p. 487(Abstract #2119), 2004.
Fuji, S., et al.; "Effect of Coadministration of Uracil or Cytosine on the Anti-Tumor Activity of Clinical Doses of 1-(2-Tetrahydrofuryl)-5-Fluorouracil and Level of 5-Fluorouracil in Rodents", Gann, vol. 70, pp. 209-214, 1979.
Fukushima, S., et al.: "Carcinogenicity of Uracil, a Nongenotoxic Chemical, in Rats and Mice and I Rationale", Cancer Research, vol. 52, pp. 188-193, 1992.
Gallo, R., et al.: "The Enzymatic Mechanisms for Deoxthymidine Synthesis in Human Leukocites", The Journal of Clinical Investigation, vol. 48, pp. 82-93, 1969.
Goodman & Gilman, The Pharmacological Basis of Therapeutics, $9^{th}$ Edition, pp. 1225-1229-, 1996.
Hageboutrous, J.M., et al.: "Life Threatening Toxicity in a Dihyropyrimidine Dehydorgenase-Deficient Patient After Treatment with Topical 5-Fluorouracil", Clinical Cancer Research, vol. 5, pp. 2006-2011, 1999.
Hartmann, H.R., et al.: "Modulation of the Effects of Fluoropyrimidines on Toxicity and Tumor Inhibition in Rodents by Uridine and Thymidine", Med. Oncol. & Tumor Pharmacother, vol. 3(2), pp. 111-118, 1986.
Hatfield, D., et al.: "Synthesis of (3-Ribosyluric Acid) 5'-Phosphate and (3-Ribosylxanthine) 5'-Phosphate by a Pyrimidine Ribonucleotide Pyrophosphorylase of Beef Erythrocytes", The Journal of Biological Chemistry, pp. 60-66, 1964.
Hejna, M., et al.: "Decrease of Duration and Symptoms in Chemotherapy-Induced Oral Mucositis by Topical GM-CSF: Results of a Prospective Randomised Trial", European Journal of Cancer, vol. 37(16), pp. 1994-2002, 2001.
Hirata, K., et al.: "Pharmacokinetic Study of S-1, A Novel Oral Fluorouracil Antiturnor Drug", Clinical Cancer Research, vol. 5, pp. 2000-2005, 1999.
Hoff, P.: "The Tegafu-Based Dihydropyrimidine Dehydrogenase Inhibitory Fluoropyrimidines, UFT/Laucovorin (ORZEL ™) and S-1: A Review of Their Clinical Development and Therapeutic Potential", Investigational New Drugs, vol. 18, pp. 153-163, 2000.
Ichikawa, W., et al.: "Polymorphins of Orotate Phosphoribosyl Transferase (OPRT) Gene and Thymidylate Synthase Tandem Repeat (TSTR) Predic t Adverse Events (AE) in Colorectal Cancer (CRC) Patients Treated with 5-Fluorouracil (FU) Pluis Leucovorin (LV)", Gastrointestinal Cancer, p. 1063, 2003.
Ichikawa, W., et al.: "Both Gene Expression for Orotate Phosphoribosyltransferase and its Ratio to Dihydropyrimidine Dehydrogenase Influence Outcome Following Fluoropyrimidine-Based Chemotherapy for Metastatic Colorectal Cancer", British Journal of Cancer, vol. 89, 2003.
Ikenaka, K., et al.: "Effect of Uracil on Metabolism of 5-Fluorouracil in Vitro", Gann, vol. 70, pp. 353-359, 1979.
Johnson, M., et al.: "Life-Threatening Toxicity in a Dihydropyrimidine Dehydrogenase-Deficient Patient after Treatment with Topical 5-Fluorouracil", Clinical Cancer Research, vol. 5, pp. 141-146, 1999.
Kawaguchi, Y., et al.: "Studies on the Metabolism of 1-(2-Tetrahydrofuryl)-5-Fluorouracil and Uracil Co-Administered Orally to Tumor-Bearing Rats", Gann, vol. 17. pp. 889-899, 1980.

Largillier, R., et al.: "Prospective Analysis of Dihydropyrimidine Dehyrodgenase (Dpd) Activity for Predicting Capecitabine-Related Toxicities in Metastatic Breast Cancer Patients", (Roser Abstract), p. 39, 2002.
Leo, S., et al.: "Dermatological Toxicity from Chemotherapy Containing 5-Fluorouracil", Journal of Chemotherapy, vol. 6(6), pp. 2-5, 1994.
Levy, S., et al.: "A Pharmacokinetic Evaluation of 0.5% and a 5% Fluorouracil Topical Cream in Patients with Actinic Keratosis", Clinical Therapeutics, vol. 23(6), pp. 908-920, 2001.
Luccioni, et al.: "Pyrimidine Nucleotide Metabolism in Human Colon Carcinomas: Comparison of Normal Tissues Primary Tumors and Zenografts", Int. J. Cancer, vol. 58, pp. 32-37, 1994.
Mackean, M., et al.: "Phase I and Pharmacologic Study of Intermittent Twice-Daily Oral Therapy with Capecitabine in Patients with Advanced and/or Metastatic Cancer", Journal of Clinical Oncology, vol. 16(9), pp. 2977-2985, 1998.
Maehara, Y., et al.: "Scientific Basis for the Combination of Tegafur with Uracil", Oncology, vol. 11(9), Supplement No. 10 pp. 14-21, 1997.
Malet-Martino, M., et al.: "Clinical Studies of Three Oral Prodrugs of 5-Fluorouracil (Capecitabine, UFT,S-1): A Review", The Oncologist, pp. 288-323, 2002.
Niedzwicki, J., et al.: "Structure-Activity Relationship of Ligands fo the Pyrimidine Nucleoside Phosphorylases", Biochemical Pharmacology, vol. 32(3), p. 399-415, 1983.
Niedzwicki, J., et al.: "Structure-Activity Relationsip of Pyrimidine Base Analogs as Ligands of Orotate Phosphoribosyltransferase", Biochemical Pharmacology, vol. 33(15), pp. 2383-2395, 1984.
Naguib, et al.: "Enzymes of Uracil Catabolism in Normal and Neoplastic Human Tissues", Cancer Research, vol. 45, pp. 5405-5412, 1985.
Powis, G.: "Anticancer Drugs: Antimetabolie Metabolism and Natural Anticancer Agents", International Encyclopedia of Pharmacology and Therapeutics, pp. 42-50, 1994.
Samid, D.: "Important Information About Xeloda (Capecitabine) Tablets", Roche Laboratories Inc. 2003.
Sawada, N., et al.: "Induction of Thymidine Phosphorylase Activity and Enhancement of Capecitabine Efficacy by Taxol/Taxotere in Human Cancer Xenografts", Clinical Cancer Research, vol. 4, pp. 1013-1019, 1998.
Schilsky, R.L., et al.: "Sixty-Third Meeting of the Oncologic Drug Advisory Committee", Food and Drug Administration Center for Drug Evaluation and Research, 1999.
Senff, H., et al.: "Topical 5-Fluorouracil Solution in the Treatment of Warts—Clinical Experience and Percutaneous Absorption", British Journal of Dermatology, vol. 118, pp. 409-414, 1988.
Sludden, J., et al.: "Liver Dihydropyrimidine Dehydrogenase Activity in Human, Cynomolgus Monkey, Rhesus Monkey, Rhesus Monkey, Dog, Rag ant Mouse", Pharmacology, pp. 276-280, 1998.
Spicer, E., et al.: "Toxicity Study of Uracil in Dogs", Journal of Applied Toxicity, vol. 5, pp. 199-204, 1985.
Stein, J.H., et al., Editor-in-Chief, Internal Medicine, $4^{th}$ Edition, Chapters 71 and 72, pp. 699-715, 1994.
Wang, J., et al.: "Oral 5-FU is a More Effective Antimetastatic Agent than UFT", Anticancer Research, vol. 24, pp. 1353-1360, 2004.
Unknown, "Lower Dose Capecitabine is Active and Has Favorable Safety Profile in Elderly Patients with Advanced Breast Cancer", Oncology News International, p. 40, 2003.
Unknown, "Xeloda (Capecitabine) Tablets Product Label Insert", Roche Pharmaceuticals, 2003.
Ford, John P., U.S. PTO Notice of Allowance, U.S. Appl. No. 12/073,424 Oct. 13, 2009, 10 pgs.
Ford, John P., U.S. PTO Office Action, U.S. Appl. No. 12/073,424, Dec. 12, 2008, 12 pgs.
Ford, John P., U.S. PTO Notice of Allowance, U.S. Appl. No. 12/071,648, Jun. 10, 2010, 12 pgs.
Ford, John P., U.S. PTO Office Action, U.S. Appl. No. 12/071,649, Jun. 30, 2009, 10 pgs.
Ford, John P., U.S. PTO Office Action, U.S. Appl. No. 12/071,648, Oct. 9, 2008, 10 pgs.
Ford, John P., U.S. PTO Notice of Allowance, U.S. Appl. No. 11/196,921, Dec. 12, 2007, 16 pgs.

(56) References Cited

OTHER PUBLICATIONS

Ford, John P., U.S. PTO Office Action, U.S. Appl. No. 11/196,921, Aug. 17, 2007, 10 pgs.
Ford, John P., U.S. PTO Office Action, U.S. Appl. No. 11/196,921, Nov. 29, 2006, 13 pgs.
Ford, John P., U.S. PTO Office Action, U.S. Appl. No. 11/146,883, May 26, 2010, 12 pgs.
Ford, John P., U.S. PTO Office Action, U.S. Appl. No. 11/146,883, Apr. 29, 2010, 7 pgs.
Ford, John P., U.S. PTO Office Action, U.S. Appl. No. 11/146,883, Aug. 17, 2009, 6 pgs.
Ford, John P., U.S. PTO Office Action, U.S. Appl. No. 11/146,883, Jul. 9, 2008, 6 pgs.
Ford, John P., U.S. PTO Office Action, U.S. Appl. No. 11/146,883, Oct. 25, 2007, 5 pgs.
Ford, John P., U.S. PTO Office Action, U.S. Appl. No. 11/146,883, Nov. 29, 2006, 5 pgs.
Ford, John P., U.S. PTO Notice of Allowance, U.S. Appl. No. 10/918,199, Sep. 16, 2005, 13 pgs.
Ford, John P., U.S. PTO Office Action U.S. Appl. No. 10/918,199, Feb. 2, 2005, 20 pgs.
Ford, John P., U.S. PTO Notice of Allowance, U.S. Appl. No. 10/684,203, Mar. 17, 2005, 9 pgs.
Ford, John P., U.S. PTO Office Action, U.S. Appl. No. 10/684,203, Dec. 8, 2004, 18 pgs.
Ford, John P., U.S. PTO Office Action, U.S. Appl. No. 10/684,203, Jun. 7, 2004, 9 pgs.
Ford, John P., U.S. PTO Office Action, U.S. Appl. No. 10/364,383, Jun. 7, 2004, 7 pgs.
Ford, John P., U.S. PTO Office Action, U.S. Appl. No. 10/364,383, Aug. 28, 2003, 7 pgs.
Office Action in related co-pending U.S. Appl. No. 11/146,883 mailed May 26, 2010.
Office Action in related co-pending U.S. Appl. No. 11/146,883 mailed Dec. 1, 2010.
Notice of Allowance in related U.S. Appl. No. 12/071,648 mailed Jun. 10, 2010.
Notice of Allowance in related U.S. Appl. No. 12/114,602 mailed Jun. 10, 2010.
Office Action in related co-pending U.S. Appl. No. 12/683,293 mailed Sep. 28, 2010.
Office Action in related co-pending U.S. Appl. No. 12/683,293 mailed Jan. 19, 2011.
Office Action in related co-pending U.S. Appl. No. 12/895,327 mailed Mar. 10, 2011.
Harvey, Stewart C.: "Drug Absorption, Action and Disposition," Chapter 35 in Remington's Pharmaceutical Sciences, 18$^{th}$ Ed., Gennaro et al. (eds.). 1990, Mack Publishing Co., Easton, PA, only pp. 697-724 supplied. See in particular pp. 712 ("Topical Route").
Harvey, Stewart C.: "Topical Drugs,"Chapter 38 in Remington's Pharmaceutical Sciences, 18$^{th}$ Ed., Gennaro et al., (eds.). 1990, Mack Publishing Co., Easton, PA, only pp. 757-773 supplied. See in particular p. 760 ("Emollients").
Zografi et al.: "Disperse Systems,", Chapter 19 in Remington's Pharmaceutical Sciences, 18$^{th}$ Ed., Gennaro et al (eds), 1990, Mack Publishing Co., Easton, PA, only pp. 257-308 supplied, See In particular p. 302 ("Emulsifying Agents").
Office Action in related co-pending U.S. Appl. No. 11/146,883 mailed Aug. 15, 2011.
Cao, et al.: "5-Fluororacil Prodrug: Role of Anabolic and Catabolic Pathway Modulation in Therapy of Colorectal Cancer," Clinical Cancer Research, vol. 1(8), pp. 839-845, 1995.
Office Action in related co-pending U.S. Appl. No. 12/883,293 mailed Dec. 16, 2011.
Office Action in related co-pending U.S. Appl. No. 12/885,327 mailed Dec. 27, 2011.
Office Action in related co-pending U.S. Appl. No. 11/146,683 mailed Feb. 28, 2012.
Final Office Action in related co-pending U.S. Appl. No. 11/146,883 mailed Dec. 14, 2012.
Non-Final Office Action issued in co-pending U.S. Appl. No. 11/146,863 mailed Feb. 6, 2014.

* cited by examiner

Clinical Effects of HFS

*"If grade 2 or 3 hand-and-foot syndrome occurs, administration of XELODA should be interrupted until the event resolves or decreases in intensity to grade 1. Following grade 3 hand-and-foot syndrome, subsequent doses of XELODA should be decreased."

(source: Roche-XELODA prescribing information)

Grading Hand-Foot Syndrome

| Grade | NCI Definition | Clinical Trial Definition | |
|---|---|---|---|
| | | Clinical | Functional |
| | Minimal skin changes or dermatitis (e.g., erythema peeling) with altered sensations (e.g., numbness, tingling, burning) but do not interfere with activities of daily living | Numbness dysesthesia/ paraesthesia, tingling, painless swelling or erythema | Discomfort that does Not disrupt normal activities |
| 2 | Skin changes present with accompanying pain interfering little with activities of daily living; skin surface remains intact | Painful erythema with swelling | Discomfort that affects activities of daily living |

Source: SM Cressett, et al. J Oncol Pharm Pract. 2006 Sept;12(3):131–41. Review.

FIG. 2

Main Side Effects of Xeloda

Table 1. Phase II trials on patients treated with capecitabine (CAP)

| Study (year) | n of evaluable patients (age), disease | CAP dose | LV dose | Response rate (95% CI) | Median duration of response (MDR); median survival time (MST) | Main side effects |
|---|---|---|---|---|---|---|
| O'Reilly et al. [77] (1998) | 22 anthracycline-resistant breast cancer | 2,510 mg/m²/d$^a$ | | 36% (17%-59%) | | |
| Blum et al. [78] (1999) | 162 paclitaxel-resistant breast cancer | 2,510 mg/m²/d$^a$ | | 20% (14%-26%) | MDR 8.1 mo MST 12.8 mo | Diarrhea, hand-foot syndrome |
| Cervantes et al. [79] (2000) | 32 taxane-resistant breast cancer | 2,500 mg/m²/d$^a$ | | 16% | | |
| Wong et al. [80] (2000) | 22 refractory breast cancer | 2,500 mg/m²/d$^a$ | | 27% | | Hand-foot syndrome |
| Watanabe et al. [81] (2001) | 55 docetaxel-resistant breast cancer | 1,657 mg/m²/d$^b$ | | 20% (10%-33%) | MDR 221 d | Hand-foot syndrome, hyperbilirubinemia |
| Blum et al. [82] (2001) | 74 taxane-resistant breast cancer | 2,510 mg/m²/d$^a$ | | 26% (16%-36%) 27% for paclitaxel-resistant patients; 20% for docetaxel-resistant patient | MDR 8.3 mo MST 12.2 mo | Hand-foot syndrome, diarrhea, stomatitis |
| Thuss-Patience et al. [83] (2001) | 100 anthracycline- and taxane-resistant breast cancer | 2,500 mg/m²/d$^a$ | | 18% | | Hand-foot syndrome, nausea, vomiting, diarrhea |

Source: The Oncologist 2002;7:288-323

FIG. 3A

Main Side Effects of Xeloda

Table 1. Phase II trials on patients treated with capecitabine (CAP)

| Study (year) | n of evaluable patients (age), disease | CAP dose | IV dose | Response rate (95% CI) | Median duration of response (MDR); medium survival time (MST) | Main side effects |
|---|---|---|---|---|---|---|
| Sundstrom et al. [84] (2000) | 7 breast cancer progressing after HDC-ASCS | 2,500 mg/m²/d$^a$ | | 71% | | Hand-foot syndrome ↓ |
| Jakob et al. [85] (2001) | 13 breast cancer progressing after HDC-ASCS | 2,500 mg/m²/d$^a$ | | 54% (26%-81%) | MST 454 d | Hand-foot syndrome ↓ granulocytopenia, nausea, diarrhea, fever |
| O'Shaughnessy et al. [86] (2001) | 61 (≥55y) untreated breast cancer | 2,510 mg/m²/d$^a$ | | 30% (19%-43%) 3 CR | MST 19.6 mo | Hand-foot syndrome ↓ diarrhea |
| Kusomo et al. [87] (2001) | 46 breast cancer | 1,657 mg/m²/d$^b$ | | 28% (16%-44%) | MDR 161 d | Hand-foot syndrome ↓ Hyperbilirubinemia |
| Procopio et al. [88] (2001) | 27 (≥65y) breast cancer | 2,500 mg/m²/d$^a$ | | 29% | | Diarrhea, vomiting, hand-foot syndrome, asthenia, stomatitis |
| Vasey et al. [89] (2000) | 15 ovarian cancer | 2,500 mg/m²/d$^a$ | | 7% | | Hand-foot syndrome ↓ diarrhea |
| Wenzel et al. [90] (2002) | 23 renal cell cancer after failing immunotherapy | 2,500 mg/m²/d$^a$ | | 9% | | Hand-foot syndrome ↓ anemia |
| Lozano et al. [91] (2000) | 55 hepatobiliary carcinoma | 2,000 mg/m²/d$^a$ | | 16% (6%-24%) | MST not reached; 1-year survival rate 70% | Hand-foot syndrome ↓ thrombocytopenia |

Source: The Oncologist 2002;7:288-323

FIG. 3B

Main Side Effects of Xeloda

Table 1. Phase II trials on patients treated with capecitabine (CAP)

| Study (year) | n of evaluable patients (age), disease | CAP dose | LV dose | Response rate (95% CI) | Median duration of response (MDR); median survival time (MST) | Main side effects |
|---|---|---|---|---|---|---|
| Cartwright et al. [92] (2002) | 42 pancreatic cancer | 2,500 mg/m²/d [a] | | 9.5% (3%–21%) | MDR 268, 260 and 566 d | Hand–foot syndrome, diarrhea, nausea |
| Hoff et al [93] (2000) | 19 5-FU-resistant colorectal cancer | 2,500 mg/m²/d [a] | | 0% | | Nausea, vomiting, diarrhea, abdominal pain |
| Van Cutsem et al. [94] (2000) | 109: colorectal cancer arm A: 39; arm B: 35; arm C: 35 | 1,331 mg/m²/d [c]; 2510 mg/m²/d [a]; 1657 mg/m²/d [a] | 60 mg/d [a] | 21% (9%–36%) 24% (11%–41%) 23% (10%–40%) | | Diarrhea, hand–foot syndrome |
| Koizumi and Taguchi [95] (2001) | 31 gastric cancer | 1,657 mg/m²/d [b] | | 19% (8%–38%) | MST 248 d | Hyperbilirubinemia, skin rash, lymphopenia |

[a] Administered orally in two daily doses for 14 days every 21 days 9 (intermittent regimen)
[b] Administered orally for 21 days every 28 days
[c] Administered orally in two daily doses every day for 12 weeks (continuous regimen)
[d] Median duration of treatment 109 days in arm A, 145 days in arm B, and 130 days in arm C, response assessed after 6 and 12 weeks of treatment
Abbreviations: LV=leucovorin, CI=confidence interval; HDC-ASCS=high-dose chemotherapy with autologous stem cell support; CR=complete response Source: The Oncologist 2002;7:288–323

FIG. 3C

Incidence of HFS

Table 2. Incidence of capecitabine-induced hand-foot syndrom in daily clinical trials

| Study | Median age | Disease | n | Capecitabine dose[b] |
|---|---|---|---|---|
| Phase II trials | | | | |
| Blum[15] | 56 | Breast cancer | 162 | 2510 mg/m² per day |
| Van Cursem[17] | A: 62 | Colorectal cancer | A: 39 | A: 1331 mg/m² per day continuously |
|  | B: 64 |  | B: 35 | B: 2510 mg/m² per day, 2 weeks on/1 week off |
|  |  |  | C: 35 | C: 1657 mg/m² per day, 2 weeks on/1 week off |
| Blum[18] | 53 | Breast cancer | 75 | 2510 mg/m² per day |
| O'Shaughnessy[16] | 69 | Breast cancer | 61 | 2510 mg/m² per day |
| Ralcharch[20] | 56 | Breast cancer | 136 | 2500 mg/m² per day |
| Gradiahar[21] | 54 | Breast cancer | 47 | 1650 mg/m² per day |
| Bejelta[12] | 73 | Breast cancer | A: 30 | 2500 mg/m² per day |
|  |  |  | B: 43 | 2000 mg/m² per day |
| Phase III trials | | | | |
| Holt[23] | 84 | Colorectal cancer | 302 | 2500 mg/m² per day |
| Van Cursem[24] | 64 | Colorectal cancer | 301 | 2500 mg/m² per day |
| O,Shaughnessy[26] | 52 | Breast cancer | 256 | 2500 mg/m² per day |
| Miller[26] | 62 | Breast cancer | 215 | 2500 mg/m² per day |
| Twelvas[27 29] | 82 | Colorectal cancer | 995 | 2500 mg/m² per day |
| Produced-dose trials | | | | |
| El-Helw[25] | 48 | Breast cancer | 57 | 1000 mg/m² per day |
| Trials in the elderly | | | | |
| Felu[20] | 76 | Colorectal cancer | 51 | 2500 mg/m² per day |
| Retrospective review | | | | |
| Hennessy[31] | 53 | Breast cancer | A: 51 | A: 2500±5% mg/m² per day |
|  |  |  | B: 16 | B: 2250±5% mg/m² per day |
|  |  |  | C: 39 | C: <2000±5% mg/m² per day |

[a] Adjustment study.
[b] All daily does were divided twice daily with 2 weeks on followd by 1 week off, unless otherwise specified.
[c] All tricls used the clinical trial specific scale unless otherwise noted (see Table 1).
[d] The National Cancer Institute Common Toxicity Criteria version 2.0 (see Table 1).
  NR, not responded bid, twice daily.

FIG. 4A

Incidence of HFS

| Drugs in combination and dose | All grades[a] (%) | Grade 3/4 (%) | Dose reduction (%) | Dose discontinuation (%) |
|---|---|---|---|---|
| — | 58 | 10 | NR | NR |
| — | 33 | 10 | NR | 7 |
| — | 45 | 15 | NR | 6 |
| Laucovorin 30 mg bid | 54 | 23 | NR | 5 |
| — | 62 | 22 | NR | NR |
| — | 43 | 15 | NR | NR |
| — | 55 | 13 | NR | 8 |
| Paclitaxel 175 mg/m² Iv on day 1 of each 21-day cycle | 49 | 11 | NR | 9 |
| — | 47 | 0 | 14 | 0 |
| — | 37 | 2 | 0 | 0 |
| — | 56 | 18 | NR | <2 |
| — | 48 | 16 | NR | <2 |
| Docataxel 75 mg/m² on day 1 of each cycle | 63 | 24 | NR | NR |
| — | 60 | 24 | NR | NR |
| — | 62 | 18 | 31 | 3 |
| — | 32 | 2 | NR | 0 |
| — | 28 | 6 | NR | NR |
| — | 74% overall for all groups[d] | 33 | NR | NR |
| — | | 63 | NR | NR |
| — | | 20 | NR | NR |

Source: J Oncol Pharm Pract 2006; 12; 131

FIG. 4B

Treatment Options for HFS

"Dose modifications, as detailed in Table 3, remain the mainstay for the management of capecitabine-induced HFS"

Table 3. Recommended dose modification with capecitabine monotherapy[a]

| Toxicity grades | During dose level | Dose adjustment for next treatment (% of starting dose) |
|---|---|---|
| Grade 1 | Maintain dose level | Maintain dose level |
| Grade 2 | | |
| First appearance | Interrupt until resolved to grade 0-1 | 100% |
| Second appearance | Interrupt until resolved to grade 0-1 | 75% |
| Third appearance | Interrupt until resolved to grade 0-1 | 50% |
| Fourth appearance | Discontinue treatment permanently | — |
| Grade 3 | | |
| First appearance | Interrupt until resolved to grade 0-1 | 75% |
| Second appearance | Interrupt until resolved to grade 0-1 | 50% |
| Third appearance | Discontinue treatment permanently | — |
| Grade 4 | | |
| First appearance | Discontinue permanently OR if physician deems it to be in the patient's best interest to continue, interrupt until resolved to grade 0-1 | 50% |

[a] Adapted from package insert   Source: J Oncol Pharm Pract 2006; 12; 131

FIG. 5

COMPOSITIONS AND METHODS FOR TREATING AND PREVENTING DERMATOSES

1. CROSS REFERENCE TO RELATED APPLICATIONS

This application is a continuation of U.S. application Ser. No. 12/893,692, filed Sep. 29, 2010, which issued as U.S. Pat. No. 8,258,147, which is a continuation of U.S. application Set. No. 12/114,602, filed on May 2, 2008, which issued as U.S. Pat. No. 7,816,366, which application is a continuation of U.S. application Set. No. 12/073,424, filed Mar. 5, 2008, which issued as U.S. Pat. No. 7,816,366, which is a continuation of U.S. application Ser. No. 11/196,921, filed on Aug. 3, 2005, which issued as U.S. Pat. No. 7,368,456, which is a continuation of U.S. patent application Ser. No. 10/918,199, filed on Aug. 13, 2004, which issued as U.S. Pat. No. 6,995,165, which is a continuation-in-part of U.S. application Ser. No. 10/684,203, flied Oct. 10, 2003, which issued as U.S. Pat. No. 6,979,688, which is a continuation-in-part of U.S. application Ser. No. 10/364,383, filed Feb. 12, 2003, which was abandoned, which claims the benefit of U.S. provisional application No. 60/355,764, filed Feb. 12, 2002, the disclosures of which are incorporated herein by reference in their entireties.

2. FIELD OF THE INVENTION

The invention encompasses compositions and methods of treating or preventing various dermatoses using compositions or formulations including uracil or a metabolite thereof.

3. BACKGROUND OF THE INVENTION 3.1 Dermatoses Related to Cancer Treatment

Systemic administration of antineoplastic chemical agents has been a mainstay of cancer treatment for the past 50 years. But despite success against an ever greater number of cancers, systemic administration of these toxic agents is often attended by deleterious side-effects that limit their clinical usefulness. The anti-metabolite fluorinated pyrimidines, among the earliest-introduced of the chemotherapeutic agents, remain front-line treatment for a variety of cancers 40 years after their clinical introduction.

The prototype is 5-fluorouracil (5-FU), which is typically administered parenterally, either by bolus or continuous infusion. Oral administration of 5-FU is disfavored due to the high activity in the gut wall of dihydropyrimidine dehydrogenase (DPD), the rate-limiting enzyme in 5-FU catabolism. To bypass this problem, orally administrable fluoropyrimidine derivatives have been developed, either in the form of 5-FU precursors, or "prodrugs" (e.g., tegafur, Carmofur, capecitabine, and doxifluridine), or as coadministered combinations of prodrugs with DPD competitors or inhibitors (e.g., UFT, S-1, or Emitefur). Tegafur (FTORAFUR®) (1-(2-tetrahydrofuryl)-5-fluorouracil), is a congener of fluoruracil that introduces a tetrahydrofuran residue in place of the deoxyribose residue in the 5'-deoxy-5-fluorouridine (5'-FUDR) molecule. Carmofur, another orally administrable fluoropyrimidine prodrug, is 1-hexylcarbamoyl-5-fluorouracil (also known as HCFU) Capecitabine (XELODA®, Roche Pharmaceuticals) is a rationally designed fluoropyrimidine carbamate prodrug of 5'-FUDR that can be given orally.

With reference to FIG. 1, tegafur, administered orally, is converted in the liver to 5-fluorouracil ("FU") by action of cytochrome P450.

Capecitabine is converted to 5-FU in a multistep process. In the liver, a 60 kDa carboxyesterase hydrolyzes much of the compound to 5'-deoxy-5-fluorocyidine (5'-DFCR). Cytidine deaminase, an enzyme found in most tissues, including tumors, subsequently converts 5'-DFCR to 5'-deoxy-5-fluorourdine (5'-DFUR). The enzyme thymidine phosphorylase (TP) then hydrolyzes 5'-DFUR to the active drug 5-FU.

Within the cell, —FU can be converted to cytostatic (and/or cytotoxic) metabolites by any one or more of three main "anabolic" pathways, each catalyzed by a different enzyme. As labeled in FIG. 1, pathway involves the action of orotate phosphoribosyl transferase (OPRT), pathway 2 activates 5-FU via uridine phosphorylase (UP), and pathway 3 requires the enzyme thymidine phosphorylase (TP). These three pathways interconnect, converging on two principal mechanisms of cell toxicity.

In the first, circled and labeled "a" at the right of FIG. 1, 5-FU is ultimately metabolized to 5-FUTP, which is incorporated during transcription into RNA. Currently, it is thought that the toxicity results from the accumulation of fluorouracil residues in a wide variety of mRNAs coding for many different proteins, rather than from alteration of any single cellular function.

The second principal mechanism of cell toxicity results from anabolic activation of 5-FU to 5-FdUMP. As circled and labeled "b" in FIG. 1, 5-FdUMP forms a ternary complex with thymidine synthase (TS) and the cofactor 5,10-methylene tetrahydrofolate ($CH_2THF$). Tight complexation sequesters TS, preventing the TS-mediated enzymatic formation of dTMP; this, in turn, decreases the synthesis, and thus availability, of thymidine triphosphate (dTTP), which is required for DNA replication and repair. Depletion of dTTP acts as a cytostatic brake on cell growth and division; more recently, it has been suggested that depletion of dTTP may directly trigger programmed cell death (apoptotic) pathways.

Catabolic inactivation of 5-FU is conceptually simpler than anabolic activation, with greater than 80% of an injected dose of 5-FU rapidly degraded by a single pathway, the first and rate-limiting step of which is catalyzed by dihydropyrimidine dehydrogenase (DPD) (also known, synonymously, as uracil reductase, dihydrouracil dehydrogenase, and as dihydrothymine dehydrogenase). The principal byproduct of catabolism, F-β-alanine, is circled and labeled "c" in FIG. 1.

Given the complex interrelatedness of the metabolic pathways, the clinical efficacy of 5-FU and its orally-administrable prodrugs depends, to a first, crude, approximation on the relative activities of the DPD-mediated catabolic pathway and each of the three principal anabolic pathways. But despite intensive study, the extent to which any of these pathways predominates in human tumors is unknown and is likely to vary across tumor types and with different modes and doses of drug administration. Malet-Martino et al., *The Oncologist* 7:288 323 (2002); Ichikawa et al., Brit. J. Cancer 89:1486 1492 (2003).

The situation becomes more complex when considering the concurrent and interacting effects of multiple, competing, substrates on the multiple and competing catabolic and anabolic enzymes in the fluoropyrimidine pathway. Further complexity is added by variation in the activity of these enzymes among a genetically diverse human population, with plasma levels of 5-FU varying by about three orders of magnitude among humans exposed to the same dose of 5-FU.

UFT is a combination of uracil and ftorafur in a 4:1 molar ratio. UFT is approved for clinical use in Europe and Japan; it has been denied FDA approval for clinical marketing in the United States.

After oral ingestion, the ftorafur component of UFT is metabolized by P450 to 5-FU. The uracil component is intended to compete with 5-FU for degradation by DPD; present at a several-fold molar excess over ftorafur in the administered composition, and thus intended to be present at a several-fold molar excess over ftorafur (and thus 5-FU) in tissues, uracil is intended to outcompete 5-FU for reaction with DPD, inhibiting DPD catabolic inactivation of 5-FU. The intended result is a higher circulating level of 5-FU, leading to greater 5-FU-mediated cytotoxicity. Cao et al., Clinical Cancer Res., 1:839 845 (1995).

But the actual in vivo concentrations of uracil and 5-FU after UFT administration do not invariably follow the intended ratio. Administration of UFT to rats results in a greater than 1000-fold variation in uracil level within various organs, and can lead to up to a 100-fold excess of uracil over 5-FU in some tissues. (Kawaguchi et al., Gann. 71(6):889 99. (1980)).

Furthermore, uracil can also compete with 5-FU for reaction with the three principal anabolic activating enzymes. In order for the UFT combination to show greater clinical efficacy than ftorafur alone, uracil must not outcompete 5-FU for activation by at least one of OPRT, TP, and UP in the tumor. The outcome thus depends upon the relative amount of each of the four principal rate-limiting enzymes in each of the cells and tissues taking up 5-FU, and on the relative affinity of each of the enzymes for uracil and 5-FU. The latter depends, in turn, at least in part on cellular pH: OPRT, for example, favors 5-FU over uracil by about 50 times at neutral pH.

Variation in the relative amounts of each of the four principal rate-limiting enzymes among tissues and tumors makes a priori prediction of UFT efficacy in any particular tumor unreliable. And experiments in laboratory animals provide little help: the relative affinities of these enzymes for 5-FU and for uracil differ substantially among different animal species, and particularly among different animal tumors.

Sludden et al. report, for example, that liver DPD activity is highly variable within and among tested species. Sludden et al., Pharmacology 56:276 280 (1998). At least one study reports that 5-fluorouracil is a better substrate for human dihydrouracil dehydrogenase (DPD) than is uracil, Naguib et al., Cancer Research, 45:5405 5412 (1985).

And a complex as the physiology of fluoropyrimidine metabolism may be with respect to desired antitumor effects, the pathophysiology of fluoropyrimidine side-effects is even less well understood.

Among these poorly understood side effects of fluoropyrimidine administration, the physiology of hand-foot syndrome ("HFS," "palmar-plantar erythrodysesthesia," "PPES") is perhaps the most obscure.

HFS usually starts with numbness, tingling, redness, and painless swelling of the hands and/or feet. Grade 1 HFS is characterized by any of numbness, dysesthesia/parasthesia, tingling, and/or painless swelling or erythema of the distal extremities. Grade 2 is defined as painful erythema of the hands and/or feet and/or discomfort affecting the patients activities of daily living. Grade 3 HFS is defined as moist desquamation, ulceration, and blistering or severe pain of the hands and/or feet and/or severe discomfort that causes the patient to be unable to work or perform activities of daily living.

HFS is progressive with dose and duration of exposure to fluoropyrimidines. The FDA-approved XELODA® product insert reports a 54% 67% incidence of HFS irrespective of grade during treatment with capecitabine at the FDA-approved dose, with a grade 3 incidence of 11 17%. HFS is also seen in treatment with other chemotherapeutic agents, including antimetabolites such as cytarabine, and agents of other classes, such as docetaxel and doxorubicin, including pegylated liposomal forms of doxorubicin (CAELYX®).

The pathophysiology of hand-foot syndrome is as yet unknown and variously ascribed to metabolites of 5-FU, local drug accumulation, increased levels of anabolic enzymes in the affected tissues, and various other factors. See, for example, Childress and Lokich, Amer. J. Clinical Oncology 26:4356 (1994); Elasmar et al., Jpn J. Clin. Oncol. 31:172 174 (2001); and Fischel et al., "Experimental arguments for a better understanding of hand-foot syndrome under capecitabine," Proc. Amer. Ass'n Cancer Res. 45:487 (abstract #2119) (March 2004).

In the face of such mechanistic uncertainty, the current standard of practice is to cease or attenuate the dose of fluoropyrimidine when hand-foot syndrome develops. Unfortunately, the severity of hand-foot syndrome appears to correlate with tumor response, Chua et al., "Efficacy of capecitabine monotherapy in patients with recurrent and metastatic nasopharyngeal carcinoma pretreated with platinum-based chemotherapy," Proc. Am. Soc. Clin. Oncol. 22:511 (abstr. 2055) (2003); dose attenuation to reduce the symptoms of hand-foot syndrome thus also reduces efficacy of rumor treatment.

Topical treatment with DMSO, which has also been proposed, see U.S. Pat. No. 6,060,083, is not typically practiced in the clinic and is of uncertain efficacy.

While hand-foot syndrome is common during capecitabine treatment, it is rarely seen with the ftorafur-containing prodrug combinations UFT and S-1. S-1 lacks uracil yet, like UFT, causes hand-foot syndrome only rarely. The reason for the disparate prevalence is unknown, with the etiology of hand-foot syndrome with S-1 administration suggested to differ from that seen with capecitabine and/or 5-FU. Elasmar et al., Jpn J. Clin. Oncol. 31:172 174 (2001).

Systemically-administered chemotherapeutic agents other than fluoropyrimidine antimetabolites also cause side effects in various organs and tissues that are not involved in the disease being treated. Many of these agents interact with, and are metabolized by, complex metabolic pathways.

There is thus a need in the art for compositions and methods for preventing and/or treating side effects of systemically administered chemotherapeutic agents.

There is a further need in the art for methods and compositions for preventing and/or treating side effects of systemically administered chemotherapeutic agents that neither abrogate nor attenuate the therapeutic effect of the systemically administered agent, thus permitting such chemotherapeutic agents to be used at therapeutic dosage levels.

There is a particular need for methods and compositions for preventing and/or treating hand-foot syndrome, including methods and compositions that would obviate the withdrawal or attenuation of the dose of systemically administered chemotherapeutic agent, thus permitting systemically administered chemotherapeutic agents, such as fluoropyrimidines, to be administered at therapeutic dosage levels.

3.2. Dermatoses

While the skin is widely regarded as an ideal barrier to protect an organism, it is also an organ in its own right and susceptible to disease and infection. Skin cancers, skin disease and skin inflammation, aside from being affected by the side effects of chemotherapy, are disruptive, if not deadly, to the organism. Furthermore, disease or inflammation of the skin can further exacerbate the dermatological side effects caused by chemotherapeutics.

Dermatoses are diseases of the skin, including cancers, viruses, bacteria, and inflammatory diseases. Dermatoses may be hereditary or brought about by contact with allergens, molds, or pollen. Dermatoses may further be caused or exacerbated by stress and fatigue. Dermatoses may be the result of deficiencies in vitamin A or result from other diseases such as diabetes. Dermatoses may include, but are not limited to, atopic dermatitis, irritant contact dermatitis, radiation-induced dermatitis, dry skin dermatitis, papulopustular rashes, xerosis, pruritis, actinic keratosis, phototoxic dermatitis, genital warts, herpes, superficial basal cell carcinoma, eczema, psoriasis, acne, tinea and ulcers.

Given the scope of underlying causes of dermatoses, most current treatments are directed to the underlying cause, such as the particular virus or bacterium. Most current treatments for dermatoses, therefore, rely on systemic administration of an agent, such as an anti-biotic or anti-viral, to treat the condition. Accordingly, current therapies rely on an accurate diagnosis in order to effectively treat the dermatosis. Furthermore, as is known in the art, disease can adapt to a treatment to resist the efficacy of the agent. For example bacteria and viruses can mutate to develop resistance to a drug. Cancers also can adapt and become inert to the effects of chemotherapeutic agents.

The use of topical agents to treat dermatoses is desirable as it places an agent at the site it is most needed without being overly invasive or suffering from systemic limitations, such as the first-pass effect with the liver. However, most topical treatments are aimed at alleviating certain symptoms and not at treating or preventing the cause of the dermatosis. Moreover, some treatments, especially ones available generally may exacerbate a particular dermatosis, especially if the dermatosis is caused by or exacerbated by a substance or allergen the subject has been exposed to.

Thus a need is felt for an effective topical agent capable of treating or preventing dermatoses that does not require an acute diagnosis. Accordingly, a single agent capable of alleviating and treating various dermatoses, regardless of the underlying cause, would be of great benefit.

The present invention provides protectant agents including uracil or a metabolite thereof that effectively prevent and/or treat the cutaneous toxicities and dermatological side-effects associated with chemotherapeutic agents. Additionally, and surprisingly, the protectant agents including uracil or a metabolite thereof provide compositions and methods for treating or preventing various dermatoses.

4. SUMMARY OF THE INVENTION

The present invention solves these and other needs in the art by providing methods, compositions, and kits for treating, preventing, or managing dermatoses including administering a therapeutically or prophylactically effective amount of uracil or a metabolite thereof.

In certain embodiments, the invention encompasses protecting organs, tissues, and/or cells (collectively hereinafter, "tissues") from the toxic effects of a systemically distributed toxic agent, such as a systemically administered chemical, biological, radiochemical, or radiobiological anticancer chemotherapeutic agent.

The invention also encompasses methods based on the asymmetric delivery of the anticancer therapeutic agent and a tissue protectant including uracil or a metabolite thereof to a subject, with the anticancer therapeutic agent delivered throughout the body, typically by systemic administration, and the protectant vectored, or targeted, to the tissue to be protected.

The invention further encompasses methods of treating or preventing side-effects caused of systemic anticancer agents by administering a composition including one or more protectant agents including uracil or a metabolite thereof to a subject in need thereof, preferably a mammal, more preferably a human. In certain embodiments, the protectant may alleviate or prevent certain side-effects from manifesting. In other embodiments, the protectant may be of use in local or topical application prior to, during, or post treatment or combinations thereof.

In another embodiment, the invention encompasses methods of treating or alleviating or preventing the onset or progression of dermatoses, including, for example, eczema, pruritis; psoriasis; acne; impetigo; warts; tinea; blisters caused by herpes simplex- and/or herpes simplex-2; atopic dermatitis; irritant contact dermatitis; radiation-induced dermatitis; dry skin dermatitis; papulopustular rashes; xerosis; actinic keratosis; genital warts; superficial basal cell carcinoma; and combinations thereof by administering a composition including uracil or a metabolite thereof to a subject in need thereof, preferably a mammal, more preferably a human.

In another embodiment, the protectant agent such as, for example, uracil or a metabolite thereof is administered so as to achieve high concentration at or within the tissue to be protected, with low to negligible systemic distribution. In another embodiment, the protectant agent such as, for example, uracil or a metabolite, thereof is administered so as to reduce the concentration of the anticancer therapeutic locally at or within the tissue to be protected. In both cases, the protectant can serve to restore normal homeostasis primarily, or exclusively, to the tissue to be protected.

In another embodiment, the protectant agent such as, for example, uracil or a metabolite thereof is administered locally, local administration being effective to establish a concentration of the protectant agent at the desired tissue that is sufficient to protect the tissue from toxicity by the systemically distributed anticancer therapeutic agent. The route of administration is chosen or adapted so as additionally to constrain the circulating concentration of the protectant agent to levels that are insufficient to abrogate the clinical efficacy of the systemically distributed anticancer therapeutic agent or metabolite.

The spatial differential in concentration achieved in the methods of the invention obviates the need to achieve a pharmacological distinction between the agents, such as a difference in affinity for one or more enzymes for which both agents serve as substrates. The methods thus permit two agents having near-identical pharmacokinetics and/or enzyme specificity or affinity to serve, respectively, as the toxic therapeutic agent and as the protectant agent such as, for example, uracil or a metabolite thereof.

The spatially directed administration of the protectant agent such as, for example, uracil or a metabolite thereof allows concentrations of the protectant to be used that might be deleterious or harmful if achieved systemically. The methods also permit an agent to be used as a protectant that would, if administered systemically, diminish or abrogate the clinical efficacy of the systemically distributed anticancer therapeutic agent.

In embodiments of the methods of the invention in which the protectant agent is, in current clinical practice, coadministered with the anti-cancer agent to achieve a systemic effect, the method comprises dissociating the routes of administration of the two agents, administering the anti-cancer agent by means sufficient to achieve systemic distribution—such as by enteral or parenteral systemic administration—and administering the protectant agent such as, for example, uracil or a metabolite thereof in a spatially directed fashion.

The protectant agent such as, for example, uracil or a metabolite thereof itself can usefully be a substrate, often biologically active, for one or more enzymes involved in the metabolic activation of the systemically distributed toxic agent. The protectant, in other alternative embodiments, can physically reduce, remove or inactive the anticancer therapeutic at the tissue or organ to be protected.

Accordingly, in another embodiment, the invention encompasses methods of protecting a desired body tissue from toxic effects of one or more systemically distributed anti-cancer therapeutic agents or metabolites thereof. The method comprises targeting one or more protectant agents for nonsystemic delivery to the tissue desired to be protected.

In other embodiments, targeted nonsystemic delivery includes administering one or more protectant agents so as to establish a local concentration of the protectant agent such as, for example, uracil or a metabolite thereof in the tissue desired to be protected that is sufficient to protect the tissue from the toxic effects of the systemic agent. Administration is performed so as additionally to ensure that the circulating concentration of the protectant agents is insufficient to abrogate the clinical efficacy of the systemically distributed anticancer therapeutic agent or metabolite at a tissue desired to be treated.

In typical embodiments, the systemically distributed anticancer therapeutic agent, or a metabolite or precursor thereof, is systemically administered, for example by parenteral administration, such as by intravenous administration, or enteral administration, such as orally.

In these embodiments, typically the protectant agent is administered locally to the desired tissue, such as by topical administration to an integumentary surface, such as skin.

The timing of administration of the protectant can vary.

In other embodiments, the one or more protectant agents such as, for example, uracil or a metabolite thereof is administered before the at-risk tissue manifests toxic effects from the systemically distributed anticancer therapeutic agent or metabolite thereof, at times even before systemic administration of the anticancer therapeutic agent (or metabolite or precursor thereof). In various embodiments, the one or more protectant agents is administered concurrently with systemic administration of the anticancer therapeutic agent. In some embodiments, the protectant is administered before, during, and after systemic administration of the anticancer therapeutic agent.

In other embodiments of the methods of the invention, the local concentration of each of the one or more protectant agents such as, for example, uracil or a metabolite thereof is at least about 5-fold greater than the circulating concentration of the protectant agent, often at least about 10-fold greater than the circulating concentration of said protectant agent, at times at least about 100-fold greater even at least about 1000-fold greater than that in the circulation.

In some embodiments, at least one of the at protectant agents such as, for example, uracil or a metabolite thereof inhibits in vivo activation of the systemically administered anticancer therapeutic agent or metabolite or precursor thereof, for example by inhibiting its anabolism. At least one of the at least one protectant agents can, for example, be a substrate for an enzyme involved in anabolic activation of the systemically administered anticancer therapeutic agent, or a metabolite or precursor thereof.

In other embodiments, at least one of the protectant agents such as, for example, uracil or a metabolite thereof facilitates in vivo catabolism of the systemically administered anticancer therapeutic agent, or a metabolite or precursor thereof.

The anticancer therapeutic agent, metabolite or precursor thereof, can be an anti-metabolite, such as a nucleotide, a nucleoside, or a derivative, analogue, or precursor thereof. For example, the systemically distributed (typically, systemically administered) anticancer therapeutic agent can be ara-C (cytarabine) or a fluoropyrimidine. The fluoropyrimidine can be parenterally administrable fluoropyrimidines and/or orally administrable.

In some embodiments, the fluoropyrimidine is 5-FU or a 5-FU prodrug such as ftorafur, doxifluridine, and capecitabine. The systemically administered fluoropyrimidine or fluoropyrimidine prodrug can be composited with an inhibitor of dihydropyrimidine dehydrogenase (DPD). Among such compositions is a composition comprising ftorafur, 5-chloro-2,4-dihydroxypyridine, and oxonic acid.

In other embodiments, the systemically distributed (typically, systemically administered) anticancer therapeutic agent, or metabolite or precursor thereof, can be an anthracycline, or a topoisomerase I inhibitor, or an antagonist of EGF or VEGF. For example, the systemically distributed agent can be an anthracycline selected from the group consisting of doxorubicin, nonpegylated liposomal doxorubicin, pegylated liposomal doxorubicin, daunorubicin, liposomal daunorubicin, epirubicin, and idarubicin.

The systemically distributed (typically, systemically administered) anticancer therapeutic agent can be associated with toxicity to an epithelium, such as an integumentary or mucosal epithelium.

In certain embodiments, the toxicity is hand-foot syndrome. In these embodiments, the protectant agent such as, for example, uracil or a metabolite thereof is usefully administered topically to the palmar and/or plantar skin surface. In embodiments in which hand-foot syndrome is caused by systemic administration of a fluoropyrimidine, such as 5-FU or capecitabine, at least one of said at least one protectant agents is usefully uracil, usefully composited in a hydrophilic ointment for topical administration to the skin of the hands and feet.

In other embodiments, the protectant is useful for treatment of cutaneous toxicities arising from epidermal growth factor inhibition (eg, Erbitux®) including papulopustular rashes, xerosis and pruritus, and combinations thereof.

In other embodiments of the methods of the invention, the targeted nonsystemic delivery of protectant agents such as, for example, uracil or a metabolite thereof includes administering the protectant agent so as to effect a reduction, in the tissue desired to be protected, in the concentration of the systemically distributed anticancer therapeutic agent (or metabolite thereof) that is sufficient to protect the tissue from the toxic effects of the systemic agent. The circulating concentration of the protectant agents is insufficient to abrogate the clinical efficacy of the systemically distributed anticancer therapeutic agent or metabolite at a tissue desired to be treated.

The methods of the present invention can sufficiently protect the at-risk tissue as to permit the full, unattenuated dose of anticancer therapeutic agent to be administered with neither dose interruption, cessation, nor attenuation.

Thus, in another embodiment the invention provides a method of treating neoplasia.

The method comprises: systemically administering an anticancer therapeutic agent, or a precursor or metabolite thereof, to a subject in need thereof; and concurrently targeting one or more protectant agents for nonsystemic delivery to the tissue desired to be protected by any of the methods above-described.

For example, the method can include the concurrent administration of one or more protectant agents such as, for example, uracil or a metabolite thereof so as to establish a local concentration of the protectant agents in the tissue desired to be protected that is sufficient to protect the tissue from the toxic effects of the systemic agent. Administration is performed so as additionally to ensure that the circulating concentration of the protectant agents is insufficient to abrogate the clinical efficacy of the systemically distributed anticancer therapeutic agent or metabolite at a tissue desired to be treated.

In other embodiments, the method can comprise the concurrent administration of one or more protectant agents such as, for example, uracil or a metabolite thereof so as to effect a reduction, in the tissue desired to be protected, in the concentration of the systemically distributed anticancer therapeutic agent (or metabolite thereof) that is sufficient to protect the tissue from the toxic effects of the systemic agent. The circulating concentration of the protectant agents is insufficient to abrogate the clinical efficacy of the systemically distributed anticancer therapeutic agent or metabolite at a tissue desired to be treated.

The systemically administered anticancer therapeutic agent, precursor or metabolite thereof can be an antimetabolite, such a fluoropyrimidine, including parenterally administrable and orally administrable fluoropyrimidines, such as 5-FU, ftorafur, Carmofur, capecitabine, doxifluridine, UFT, S-1, or Emitefur.

In such embodiments, at least one of the at least one protectant agents such as, for example, uracil or a metabolite thereof concurrently administered with the fluompyimidine can be uracil. The uracil can, for example, be administered topically to the plantar and/or palmar skin surfaces.

In another aspect, the invention encompasses pharmaceutical compositions for local application to a body tissue, the composition capable of establishing a local concentration of one or more protectant agents such as, for example, uracil or a metabolite thereof sufficient to protect the tissue from toxic effects of one or more systemically distributed anticancer therapeutic agents or metabolites thereof without abrogating the clinical efficacy of said systemically distributed anticancer therapeutic agent or metabolite. The composition includes at least one protectant agent such as, for example, uracil or a metabolite thereof; and a pharmaceutically acceptable carrier suitable for local application.

In some embodiments, at least one of the at least one protectants in the composition is uracil. Uracil can be present within the composition at a concentration by weight of at least about 0.01 wt. %, often at least about 0.1 wt. %, even at least about 1.0 wt. %. In various embodiments, uracil can be present within at a concentration by weight of no more than about 60 wt. %, often at a concentration of no more than about wt. 5%.

In yet a further embodiment, the invention encompasses kits for oral delivery of an anticancer therapeutic agent or precursor ("prodrug") thereof with reduced toxicity to a desired tissue.

The kit includes at least one dose of an orally administrable anticancer therapeutic agent or precursor thereof; and at least one dose of a locally administrable tissue protectant composition. In some embodiments, the orally administrable anticancer therapeutic agent or precursor is a fluoropyrimidine or fluoropyrimidine composition, such as ftorafur, Carmofur, capecitabine, doxifluridine, UFT, S-1, or Emitefur.

In kits, the fluoropyrimidine is capecitabine, the protectant agent is uracil or a metabolite thereof composition and the protectant is suitable for topical delivery to the skin. The uracil can usefully be present at a concentration by weight of at least about 0.1%, even at least about 1.0%. The uracil can be present within the composition at a concentration by weight of no more than about 60%, even no more than about 10%, with uracil usefully present in a weight percentage of about 0.11% 10%, even 1% 5%.

5. BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIG. 2 shows a summary of the clinical effects seen in the various grades of sand and Foot Syndrome.

FIGS. 3A-3D show examples of the incidence Hand and Foot syndrome occurs when treating various cancers with varying doses of Xeloda®.

FIG. 4 shows the incidence of Hand and Foot syndrome in clinical trials for capecitabine.

FIG. 5 shows the approach to modifying capecitabine dosing based on the grade of Hand and Foot syndrome.

6. DETAILED DESCRIPTION OF THE INVENTION

6.1 Compositions of the Invention

Figure 1:
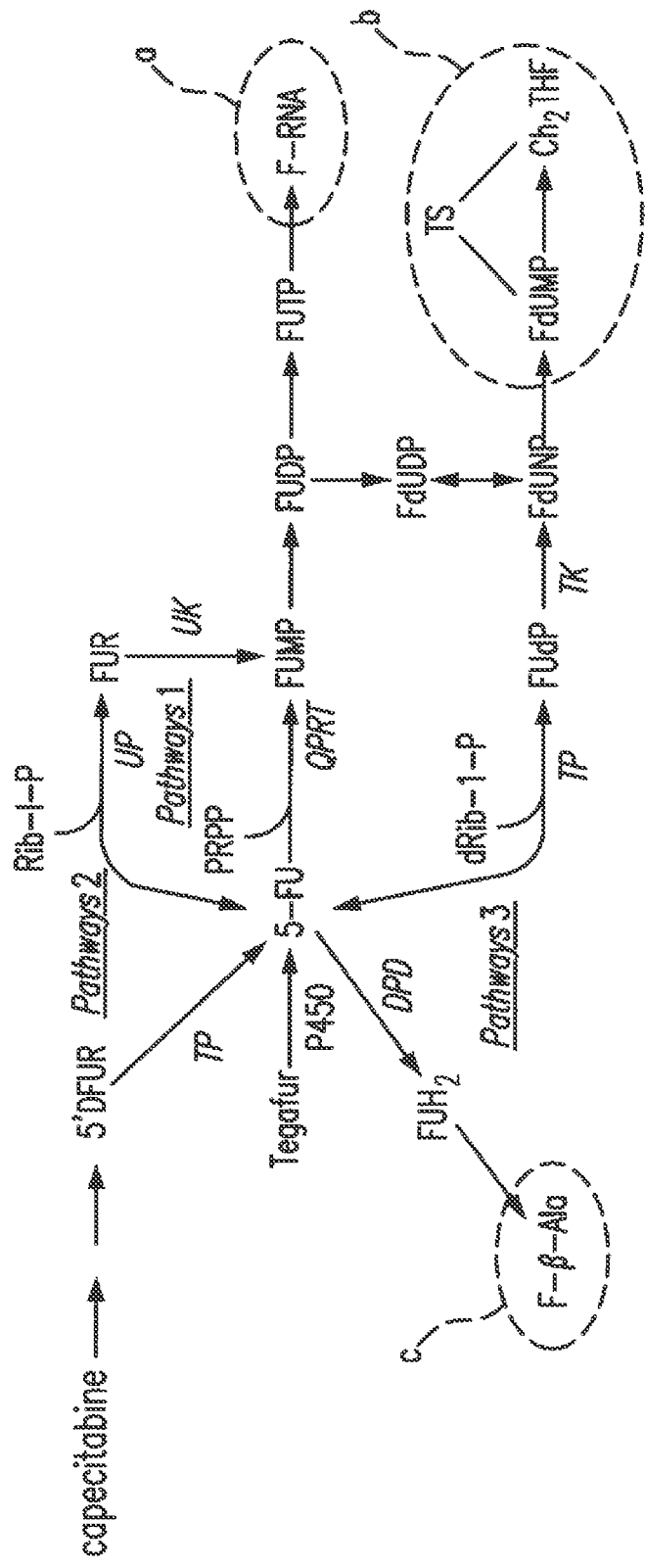
FIG. 1 shows the basic metabolic pathways for anabolic activation and catabolic degradation of fluoropyrimidines.

The invention encompasses compositions and formulations that are useful in treating, preventing or managing various dermatoses. In certain embodiments, the compositions include at least one protectant agent including, for example, uracil. Uracil can be included within the composition at a concentration by weight of at least about 0.01%, often at least about 0.1%, even at least about 1.0% various embodiments, uracil can be present within at a concentration by weight of no more than about 60%, often at a concentration of no more than about 5%.

As used herein, "Compositions" or "Compositions" of the invention refers to a composition including a therapeutically or prophylactically effective amount of uracil or a metabolite thereof.

Uracil (or thymine) is a pyrmidine and metabolizes according to the metabolic pathways in FIG. 7. Accordingly, in certain embodiments the compositions and formulations of the invention include a metabolite of uracil.

Accordingly, a metabolite of uracil or a uracil analog may act as a protectant. The oxidative pathway resulting urea or derivative thereof and malonic acid or derivatives thereof may provide beneficial effects to the local area. The topical presence or production of urea may, for example, rehydrate the epithelium. This is of use, for example, in relieving radiation-induced dermatitis. The presence or production of malonic acid or malonate and derivatives thereof may inhibit cell adhesion and inhibit inflammation. Such effects are of use in disorders or side effects including arthritis, asthma, and psoriasis.

In other embodiments, the compositions can include, for example, a naturally occurring compound, such as a compound that serves as a substrate for any one or more of TP, UP, and OPT. The compound can be a naturally occurring nitrogenous base, such as a pyrimidine, including uracil or metabolites thereof. In other embodiments, the compound can be a non-naturally occurring nitrogenous base, such as a normaturally occurring pyrimidine.

Typically, the agents in the compositions will not act as an irreversible inhibitor of or otherwise interfere with an enzymatic activity or pathway in the cell, and thus will not occasion an imbalance in the absolute and relative nucleotide concentrations within the cell.

In other embodiments, the compositions can be one that facilitates in vivo catabolism of the systemically administered anticancer therapeutic agent, metabolite, or precursor thereof.

In other embodiments, the compositions are suitable for administration locally to the tissue desired to be protected. In some such embodiments, the compositions are administered topically to the tissue desired to be protected. In ether such embodiments, the compositions are administered by local injection, such as by local injection of a depotized form of the one or more protectant agents, including for example, uracil or a metabolite thereof.

The compositions may be administered using a variety of dosage schedules designed to establish and maintain a local concentration in the tissue desired to be protected that is sufficient to protect the tissue from the toxic effects of the systemically distributed anticancer therapeutic agent or anticancer therapeutic agent metabolite, yet constrain the circulating concentration of protectant to levels that are insufficient to abrogate the clinical efficacy of the systemically distributed anticancer therapeutic agent or metabolite.

The exact dosage schedule will depend, inter alia, on any one or more of the identity of the systemically distributed chemotherapeutic agent or metabolite, the circulating concentration of chemotherapeutic agent or metabolite, the tissue desired to be treated, the severity of side effects desired to be prevented or treated, and the formulation of the active agent in the composition, particularly its concentration in the composition; determination of the proper dosage schedule of active agent is within the skill of the clinical artisan.

For example, in embodiments of the methods of the invention in which the composition is administered topically to skin in an ointment, the uracil or a metabolite thereof can usefully be administered once a day, twice a day, three times a day, four times a day, or more times a day. As would be understood in the art, the composition can be applied with different dosage schedules to different tissues of a single patient. For example, the composition may be applied twice a day to the area in need, for example the plantar surface of the feet, but applied more frequently to the hands, such as after each washing of the hands. The exact schedule may vary by patient.

In some embodiments, the amount of uracil or metabolite thereof administered per dose is at least 0.01 g, 0.02 g, 0.03 g, 0.04 g, 0.0 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3 g, 4 g, even 5 g or more, with intermediate values permissible. Typically, the amount of uracil or metabolite thereof administered per dose is no more than about 10 g, 9 g, 8 g, 7 g, 6 g, even no more than about 5 g, 4.5 g, 4 g, 3.5 g, 3 g, 2 g, 1 g, and in certain embodiments even no more than about 0.5 g, 0.4 g, 0.3 g 0.2 g, even no more than about 0.1 g.

For example, in embodiments of the compositions in which uracil as the protectant agent is administered two to four times per day to the palmar and/or plantar surfaces of a patient undergoing systemic administration of an anticancer therapeutic agent, prodrug or metabolite thereof, such as systemic administration of a fluoropyrimidine, such as 5-FU or capecitabine, the amount of uracil administered per dose can usefully be at least about 0.01 g, 0.02 g, 0.03 g. 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, even at least 1.0 g, and typically no more than about 2.0 g, 1.5 g, 1.0 g, 0.9 g, 0.8 g. 0.7 g, 0.6 g, 0.5 g, 0.4 g, 0.3 g, 0.2 g, with a dose of 0.1 g currently preferred.

In another aspect, the invention provides protectant agents, including for example uracil or metabolite thereof formulated in compositions that permit local concentrations of protectant to be established that are sufficient to protect the tissue from the toxic effects of the systemically distributed anticancer therapeutic agent or anticancer therapeutic agent metabolite, yet constrain the circulating concentration of protectant to levels that are insufficient to abrogate the clinical efficacy of the systemically distributed anticancer therapeutic agent or metabolite.

Compositions of the present invention comprise one or more protectant agents such as uracil or metabolite thereof and at least one pharmaceutically acceptable carrier or excipient.

Each of the at least one protectant agents such as uracil or metabolite thereof is typically present in the protectant composition to a weight/weight percentage of at least 0.01%, 0.05%, 1.0%, 1.5%, 2.0%, 2.5%, 3.5%, 4.0%, 4.5%, 5.0%, 10%, 15%, 20%, 25%, 30%, 35%, 40%, 45%, 50%, 55%, 60%, 65%, 70%, 75%, even 80% or more, with intermediate values permissible, and is typically present to a weight/weight percentage of no more than about 80%, 75%, 70%, 65%, 60%, 55%, 50%, 45%, 40% 30%, 35%, 30%, 25%, 20%, 15%, 10%, 5%, 45%, 4.0%, 3.5%, 3.0%, 2.5%, 2.0%, 1.5%, 1.0%, and even, at times, to a weight/weight percentage of no more than about 0.05%, even as little as 0.01%.

In certain embodiments, the compositions comprise a plurality of protectant agents, typically the plurality of protectants are cumulatively present to a weight/weight percentage of at least 0.01%, 0.05%, 1.0%, 1.5%, 2.0%, 2.5%, 3.5%, 4.0%, 4.5%, 5.0%, 10%, 15%, 20%, 25%, 30%, 35%, 40%, 45%, 50%, 55%, 60%, 60%, 65%, 70%, 75%, even 80% or more, with intermediate values permissible, and is typically present to a weight/weight percentage of no more than about 80%, 75%, 70%, 65%, 60%, 55%, 50%, 45%, 40%, 35%, 30%, 25%, 20%, 15%, 10%, 5%, 4.5%, 4.0%, 3.5%, 3.0%, 2.5%, 2.0%, 1.5%, 10%, 0.05%, even as little as 0.01%, with intermediate values permissible.

In certain embodiments, the compositions are useful for treating skin surfaces for example protecting the palmar and/or plantar from hand-foot syndrome, from side-effect associated with systemic administration of a fluoropyrimidine, an anthracycline, or a taxane anticancer therapeutic agent, or metabolite or precursor thereof, the compositions of the invention typically include uracil or a metabolite thereof as the protectant agent, with the composition comprising uracil to a weight/weight percentage of at least 0.01%, 0.05%, 1.0%, 1.5%, 2.0%, 2.5%, 3.5%, 4.0%, 4.5%, 5.0%, 10%, 15%, 20%, 25%, 30%, 35%, 40%, 45%, 50%, 55%, 60%, 65%, 70%, 75%, even 80% or more, with intermediate values permissible; in such compositions, uracil is typically present to a weight/weight percentage of no more than about 80%, 75%, 70%, 65%, 60%, 55%, 50%, 45%, 40%, 35%, 30%, 25%, 20%, 15%, 10%, 5%, 4.5%, 4.0%, 3.5%, 3.0%, 2.5%, 2.0%, 1.5%, 1.0%, and even, at times, to a weight/weight percentage of no more than about 0.05%, even as little as 0.01%, with intermediate values permissible.

In preferred compositions for treating, preventing or managing skin surfaces, uracil is present to a weight/weight percentage of at least about 0.1%, 0.2%, 0.3%, 0.4%, 0.5%, 0.6%, 0.7%, 0.8%, 0.9%, even to a weight/weight percentage of at least about 1.0%, 1.1%, 1.2%, 1.3%, 1.4%, 1.5%, 1.6%, 1.7%, 1.8%, 1.9%, 2.0%, 2.5%, 3.0% or more, with intermediate values permissible. In some embodiments, uracil is present to a weight/weight percentage of at least about 3.5%, 4.0%, 4.5%, 5.0%, 10%, 15%, 20%, 25%, 30%, 35%, 40%, 40%, 50%, 55%, even at least about 60%, typically no more than about 60%, 55%, 50%, 45%, 40%, 35%, 30%, 25%, 20%, 15%, 10%, 5%, 4.5%, 40%, 35%, 3.0%, 2.5%, 2.0%, 1.5%, 1.0%, 0.05%, with intermediate values permissible. In certain useful embodiments, uracil is present to a weight/weight percentage of about 1%.

The exact formulation of the uracil compositions of the invention will depend upon the identity of the tissue desired to be protected. Pharmaceutical formulation is a well-established art, and is further described in Gennaro (ed.), *Remington: The Science and Practice of Pharmacy*, 20th ed., Lippincott, Williams & Wilkins (2000) (ISBN: 0683306472); Ansel at al., *Pharmaceutical Dosage Forms and Drug Delivery Systems*, 7th ed., Lippiacott Williams & Wilkins Publishers (1999) (ISBN: 0683305727); and Kibbe (ed.), *Handbook of Pharmaceutical Excipients American Pharmaceutical Association*, 3rd ed. (2000) (ISBN: 091733096X), the disclosures of which are incorporated herein by reference in their entireties.

Compositions of the invention intended for topical administration to the skin may, for example, be anhydrous, aqueous, or water-in-oil or oil-in-water emulsions. Emulsions are presently preferred. Compositions of the invention may further include one or more pharmaceutically acceptable carriers or excipients and various skin actives. Amounts of the carrier may range from about 1 to about 99%, preferably from about 5 to about 70%, optimally from about 10 to about 40% by weight. Among useful carriers are emollients, water, inorganic powders, foaming agents, emulsifiers, fatty alcohols, fatty acids, and combinations thereof.

Emollients can be selected from polyols, esters and hydrocarbons. Polyols suitable for the invention may include propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin, xylitol and mixtures thereof.

Esters useful as emollients include alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmirate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are C12 C15 alcohol benzoate esters.

Esters useful as emollients also include alkenyl esters of fatty acids having 10 to 20 carbon atoms. Examples thereof include oleyl myristate, oleyl stearate and oleyl oleate.

Esters useful as emollients also include ether-esters such as fatty acids esters of ethoxylated fatty alcohols.

Esters useful as emollients also include polyhydric alcohol esters. Ethylene glycol mono- and di-fatty acid esters, diethylene glycol mono- and di-fatty acid esters, polyethylene glycol (200 6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

Esters useful as emollients additionally include wax esters such as beeswax, spermaceti, myristyl myristate, stearyl stearate.

Esters useful as emollients still further include sterol esters, of which cholesterol fatty acid esters are examples thereof.

Illustrative hydrocarbon carriers are mineral oil, polyalphaolefins, petrolatum, isoparaffin, polybutenes and mixtures thereof.

Inorganic powders are also useful as carriers in the compositions of the present invention. Examples include clays (such as Montmorillonite, Hectorite, Laponite and Bentonite), talc, mica, silica, alumina, zeolites, sodium sulfate, sodium bicarbonate, sodium carbonate, calcium sulfate and mixtures thereof.

The compositions of she invention can also include aerosol propellants, serving as, or in addition to, carriers or excipients. Propellants can be based on volatile hydrocarbons such as propane, butane, isobutene, pentane, isopropane and mixtures thereof. Philips Petroleum Company is a source of such propellants under trademarks including A3, A32, A51 and A70. Halocarbons including fluorocarbons are further widely employed propellants.

The compositions of the present invention, particularly embodiments formulated for administration to the skin, can comprise emulsifiers, either serving as, or in addition to, carriers or excipients.

Emulsifiers may be selected from nonionic, anionic, cationic, or amphoteric emulsifying agents. They may range in amount anywhere from about 0.1 to about 20% by weight.

Illustrative nonionic emulsifiers are alkoxylated compounds based on C10 C22 fatty alcohols and acids and sorbitan. These materials are available, for instance, from the Shell Chemical Company under the Neodol trademark. Copolymers of polyoxypropylenepolyoxyethylene sold by the BASF Corporation under the Pluronic trademark are sometimes also useful. Alkyl polyglycosides available from the Henkel Corporation may also be utilized for purposes of this invention.

Anionic type emulsifiers include fatty acid soaps, sodium lauryl sulfate, sodium lauryl ether sulfate, alkyl benzene sulphonate, mono- and di-alkyl acid phosphates, sarcosinates, taurates and sodium fatty acyl isethionate.

Amphoteric emulsifiers useful in the compositions of the present invention include such materials as dialkylamine oxide and various types of betaines (such as cocamidopropyl betaine).

The compositions of the present invention can also include preservatives, such as methyl paraben and propyl paraben are useful to prevent microbial contamination.

In embodiments of the compositions of the present invention formulated for topical application to skin, the composition can usefully be formulated as an ointment, a cream, a lotion, a paste, an aerosol spray, a roll-on liquid, stick, or pad, or an aerosol foam (mousse) composition.

For example, mousse compositions of the present invention can be quick-breaking or slow-breaking foams, such as those described in U.S. Pat. Nos. 6,730,288, 6,627,585, 6,589,518, 6,395,258, 6,383,472, 6,113,888, 6,113,881, 6,080,392, 5,783,202, the disclosures of which are incorporated herein by reference in their entireties.

In one embodiment, the composition is a hydrophilic ointment comprising uracil as the protectant agent, and further comprising methyl paraben, propyl paraben, sodium lauryl sulfate, propylene glycol, sterol alcohol, white petrolatum, water and light mineral oil.

In embodiments in which the tissue desired to be protected is the mucosal epithelium of the mouth, as in chemotherapy-induced stomatitis, the protectant agents can be applied to the oral cavity in the form of a topical formulation. In methods of the present invention for protecting mucosal epithelium from the toxic effects of a systemically distributed anticancer therapeutic agent or metabolite thereof, care is typically taken to prevent or to reduce oral ingestion.

Formulations suitable for topical oral application include oral emulsions, magmas, gels, swishes, lozenges, pastes, creams, oral solutions, gums, etc., as are well known in the art. Any of these topical oral vehicles can be used in conjunction with the methods of the invention. Exact formulations, as well as methods of their preparation, will be apparent to those of skill in the art.

In one embodiment of a composition of the invention useful for topical delivery to the mucosal epithelium of the mouth, the one or more protectant agents are administered in a topical gel-like formulation comprising a gel-like vehicle. The gel-like vehicle generally comprises a water-soluble gelling agent, a humectant and water, and has a viscosity of about 500 to 100,000 cps, preferably about 10,000 to 50,000 cps, more preferably about 15,000 to 30,000 cps and most preferably about 20,000 to 25,000 cps as measured with a Brookfield viscometer at about 25.degree. C. The gelling agent provides the formulation with good mucoadhesion properties; the humectant with good moisturizing and moisture-barrier properties.

Gelling agents suitable for use with the vehicle of the invention include, e.g., agar, bentonite, carbomer (e.g., carbopol), water soluble cellulosic polymers (e.g., carboxyalkyl cellulose, hydrosyalkyl cellulose, alkyl cellulose, hydroxyalkyl alkylcellulose), povidone, kaolin, tragacanth and veegum, with hydroxyalkyl alkyl celluloses such as hydroxypropyl methylcelluose being preferred.

Humectants suitable for use with the gel-like vehicle of the invention include, e.g., glycerin, propylene glycol and sorbitol, with sorbitol being preferred.

Generally, the vehicle comprises about 0.1% (w/w) to 10% (w/w) water-soluble gelling agent, with about 0.25% (w/w) to 5% (w/w) being preferred and about 0.5% (w/w) to 3% (w/w) being most preferred and about 0.1% (w/w) to 20% (w/w) humectant. However, as the viscosity of the gel-like vehicle is of considerable importance, it will be understood that the above concentration ranges are for guidance only. The actual concentration of gelling agent will depend, in part on the polymer selected, the supplier and the specific lot number. The actual concentrations of other ingredients will likewise affect the viscosity of the gel-like formulation. Choosing appropriate concentrations to yield a gel-like formulation with the desirable viscosity and other properties described herein is within the capabilities of ordinarily skilled artisans.

Additionally, the gel-like vehicle of the invention may include antimicrobial preservatives. Antimicrobial preservatives useful with the compositions of the invention include, but are not limited to, antifungal preservatives such as benzoic acid, alkylparabens, sodium benzoate and sodium propionate; and antimicrobial preservatives such as benzalkonium chloride, benzethonium chloride, benzyl alcohol, cetylpyridinium chloride, chlorobutanol, phenol, phenylethyl alcohol, phenylmercuric nitrate and thimerosal, with alkylparabens such as methylparaben, propylparaben and mixtures thereof being preferred.

An amount of antimicrobial preservative(s) effective for use with the formulations of the invention will be apparent to those of skill in the art and will depend, in part, on the antimicrobial agent(s) used. Typical concentrations range from about 0.01% (w/w) to about 2% (w/w).

The composition of the invention formulated for topical administration to the oral mucosa may also contain from about 1% (w/w) to 10% (w/w) of a sweetening agent such as aspartame, dextrose, glycerin, malitol, mannitol, saccharin sodium, sorbitol, sucrose and xylitol. Such sweetening agents are believed to aid patient compliance.

The pH of the composition will depend on the tissue protectant(s) contained in the composition. Determination of an optimal pH for stability and efficacy is well within the skill of the ordinary artisan.

Other optional ingredients that can be used without deleteriously affecting, and in some cases even enhancing, the efficacy of the formulations of the invention adapted for mucosal, notably oral mucosal, delivery, include, but are not limited to, acidifying agents such as acetic acid, citric acid, fumaric acid, hydrochloric acid, tactic acid and nitric acid; alkalinizing agents such as ammonia solution, ammonium carbonate, diethanolamine, monoethanolamine, potassium hydroxide, sodium borate, sodium carbonate, sodium hydroxide, triethanolamine and trolamine; buffering agents such as potassium metaphosphate, potassium phosphate, sodium acetate and sodium citrate; antioxidants such as ascorbic acid, ascorbyl palmitate, butylated hydroxyanisole, butylated hydroxytoluene, hypophosphorous acid, monothioglyceride, propyl gallate, sodium ascorbate, sodium bisulfite, sodium formaldehyde sulfoxylate and sodium metabisulfite; chelating agents such as edetate disodium and edetic acid; colorants such as FD&C Red No. 3, FD&C Red No. 20, FD&C Yellow No. 6, FD&C Blue No. 2, D&C Green No. 5, D&C Orange No. 5, caramel and ferric oxide, red; and flavoring agents such as anise oil, cinnamon oil, cocoa, menthol, orange oil, peppermint oil vanillin. Suitable concentrations for use will be apparent to those of skill in then art. Other optional ingredients, as well as suitable concentrations for use, can be found, for example, in Gennaro (ed.), Remington: The Science and Practice of Pharmacy, 20th ed., Lippincott, Williams & Wilkins (2000) (ISBN: 0683306472).

6.2. Methods of Treating, Preventing, or Managing Dermatoses

In certain embodiments, the inventions encompass methods of treating, preventing, or managing dermatoses. During the course of testing the compositions of the invention in side-effects associated with patients undergoing chemotherapy, the inventors surprisingly and unexpectedly determined that the compositions of the invention could be useful in treating, preventing, or managing various dermatoses, in general.

6.2.1 Dermatoses Associated with Chemotherapy

Accordingly, in certain embodiments, the invention encompasses methods of protecting a desired organ or body tissue from toxic effects of one or more toxic agent, such as anticancer therapeutic agents, or metabolites thereof, that are systemically distributed through the body of a subject, typically a human patient undergoing chemotherapy for cancer. The toxic agent may be a chemical, biological, radiochemical, or radiobiological agent.

In certain embodiments, the body tissue desired to be protected may be any body tissue that is not intended to be treated by the systemically distributed anticancer therapeutic agent or anticancer therapeutic agent metabolite.

In certain embodiments, the systemically distributed anticancer therapeutic agent, or a metabolite or precursor thereof, is systemically administered, for example by parenteral administration, such as by intravenous administration, or enteral administration, such as orally.

For example, in embodiments in which the patient is being treated for cancer, the body issue desired to be protected would typically be one that does not contain neoplastic cells. Analogously, in embodiments in which the patient is being treated with an anticancer therapeutic agent (or anticancer therapeutic agent metabolite) to effect myeloablation, for example to condition the patient prior to bone marrow transplantation, the tissue desired to be protected may be any tissue other than the bone marrow.

In certain embodiments, the protectant, for example, uracil or a metabolite thereof, is of use for treating the side-effects caused by systemic anticancer agents. The protectant, for example, uracil or a metabolite thereof may alleviate or prevent certain side effects from manifesting. The protectant, for example, uracil or a metabolite thereof may be of use in local or topical application prior to, during, or post treatment or combinations thereof.

The method may comprise administering one or more protectant agents for example, uracil or a metabolite thereof to the subject.

The protectant for example, uracil or a metabolite thereof itself may further usefully be a substrate, often biologically active, for on one or more enzymes involved in the metabolic activation of the systemically distributed toxic agent. The protectant, for example, uracil or a metabolite thereof in other alternative embodiments, can physically reduce, remove or inactive the anticancer therapeutic at the tissue or organ to be protected.

In a first series of embodiments, the one or more protectant agents, for example, uracil or a metabolite thereof are so administered as to establish a local concentration of protectant agent in the organ, tissue, or cells (hereinafter, collectively "tissue") desired to be protected that is sufficient to protect the tissue from the toxic effects of the systemically distributed toxic agent, such as a systemically distributed anticancer therapeutic agent or anticancer therapeutic agent metabolite, yet also constrain the circulating concentration of protectant to levels that are insufficient to abrogate the clinical efficacy of the systemically distributed anticancer therapeutic agent or metabolite. The route of administration is chosen or adapted so as additionally to constrain the circulating concentration to levels that are insufficient to abrogate the clinical efficiency of the systemically distributed anticancer therapeutic agent or metabolite. By way of example, local concentration may be achieved by direct administration to a local area or by targeting delivery to the desired local area. Direct administration may be by injection or by topical application.

A spatial differential in concentration may be achieved in the methods of the present invention to obviate the need to achieve a pharmacological distinction between the agents, such as a difference in affinity for one or more enzymes for which both agents serve as substrates. The methods thus permit two agents having near-identical pharmacokinetics and/or enzyme specificity or affinity to serve, respectively, as the toxic therapeutic agent and as the protectant for example, uracil or a metabolite thereof.

The spatially directed administration of the protectant, for example, uracil or a metabolite thereof allows concentrations of the protectant to be used that might be deleterious or harmful if achieved systemically. The methods also permit an agent to be used as a protectant, for example, uracil or a metabolite thereof that would, if administered systemically, diminish or abrogate the clinical efficacy of the systemically distributed anticancer therapeutic agent.

In a second series of embodiments, the one or more protectant agents, for example, uracil or a metabolite thereof, are so administered as to lower the active concentration of the systemically distributed toxic agent (such as a systemically distributed anticancer therapeutic agent, or metabolite thereof) at or within the tissue desired to be protected to a level that protects the tissue from the toxic effects of the systemically distributed toxic agent, without, however, lowering the levels of the systemically distributed toxic agent, at the tissue desired to be treated, to levels that abrogate the clinical efficacy of the systemically distributed anticancer therapeutic agent or metabolite.

"Protection" intends a clinically observable decrease in one or more toxic effects in the body tissue desired to be protected, as compared to the toxic effects that would be seen absent the protectant.

Protection can be total, preventing all symptoms of toxicity in the desired tissue; protection can be partial, reducing and/or delaying development of all or a subset of symptoms of toxicity in the desired tissue. In some embodiments, protection is sufficient to permit administration of the full dose and course of intended therapy with anticancer therapeutic agent or metabolite or precursor (prodrug) without dose cessation, dose attenuation, and/or alteration in dosage schedule. In some embodiments, protection is sufficient to allow an increase in dose of the anticancer therapeutic agent or metabolite or precursor.

The circulating concentration of the one or more protectants, for example, uracil or a metabolite thereof is constrained to levels that are insufficient to abrogate the clinical efficacy of the systemically distributed anticancer therapeutic agent or metabolite thereof.

"Abrogate" intends a diminution in efficacy of the anticancer therapeutic agent (or metabolite thereof at the tissue desired to be treated that is sufficiently great as to render therapy with the anticancer therapeutic agent or anticancer therapeutic agent metabolite clinically ineffective or clinically inadvisable. In some embodiments, the circulating concentration of the one or more protectant agents is sufficiently low as to cause no clinically observable diminution in potency or efficacy of the systemically distributed anticancer therapeutic agent (or metabolite thereof) at the tissue desired to be treated, such as a tissue having neoplastic cells. In other embodiments, the circulating concentration of the one or more protectant agents causes a clinically observable diminution in potency or efficacy of the systemically distributed anticancer therapeutic agent (or metabolite) at the tissue desired be desired to be treated, but is insufficient to abrogate the clinical efficacy of the systemically distributed anticancer therapeutic agent or metabolite thereof.

In typical embodiments, the local concentration of the one or more protectants in the tissue desired to protect from toxic effects will be greater than the concentration in the circulation. In some embodiments, the circulating concentration of the one or more protectants will be greater, in turn, than their concentration in the tissues desired to be treated with the systemically distributed anticancer therapeutic agent (such as a cancerous tissue).

In some embodiments, the local concentration of each of the one or more protectant agents, for example, uracil or a metabolite thereof in the tissue desired to be protected is at least 5-fold greater than the circulating concentration of the protectant agent. In other embodiments, the local concentration is at least 10-fold, at least 20-fold, at least 30-fold, at least 40-fold, at least 50-fold or more than the concentration of the protectant in the circulation. In various embodiments, the local concentration can be as high as at least 60-fold, 70-fold, 80-fold, 90-fold, even as high as 100-fold or more greater than the concentration of the protectant in the circulation. In some embodiments, the local concentration of protectant can be as high as 1000-fold higher than in the circulation or even more.

In some embodiments, at least one of the at least one protectant agents, for example, uracil or a metabolite thereof inhibits in vivo activation of the systemically administered anticancer therapeutic agent or metabolite or precursor thereof, for example by inhibiting its anabolism. At least one of the at least one protectant agents for example, uracil or a metabolite thereof can, for example, be a substrate for an enzyme involved in anabolic activation of the systemically administered anticancer therapeutic agent, or a metabolite or precursor thereof.

In various embodiments, the local concentration of protectant, for example, uracil or a metabolite thereof in the tissue desired to be protected is at least 10-fold, at least 20-fold, at least 30-fold, at least 40-fold, at least 50-fold or more greater than the concentration of the protectant in the tissue desired to be treated. In various embodiments, the local concentration in the tissue desired to be protected can be as high as at least 60-fold, 70-fold, 80-fold, 90-fold, even as high as 100-fold or more greater than the concentration of the protectant, for example, uracil or a metabolite thereof in the tissue desired to be treated. In some embodiments, the local concentration of protectant, for example, uracil or a metabolite thereof can be as high as 1000-fold higher than in the tissue desired to be treated, or even more. The tissue desired to be treated can, for example, be a tumor within a body tissue or the entirety of a body tissue within which a portion of the cells are neoplastic.

Treatment with the protectant, for example, uracil or a metabolite thereof is useful for cutaneous toxicities. Cutaneous toxicities may include papulopustular rashes, xerosis and pruritus, which have a significant impact on health and quality of life. A majority of patients treated with agents targeting the epidermal growth factor receptor (EGFR) experience cutaneous toxicities. Biologic agents targeting EGFR are as a robust treatment option for various solid tumors, yet the cutaneous side-effects can severely affect the ability to provide a sufficient dose. Treatment with the protectant is useful for cutaneous toxicities arising from epidermal growth factor inhibition (e.g., Erbitux®), including papulopustular rashes, xerosis and pruritus.

In certain embodiments in which the tissue desired to be protected is the skin, for example, the one or more protectant agents will typically be formulated for localized, typically topical, administration to the skin surface. In embodiments in which the patient is being treated systemically with a fluero-pyrimidine, an anthiracycline, or a taxane anticancer therapeutic agent, or precursor or metabolite thereof, for example, the one or more protectant agents will often be formulated for topical administration to the palmar and planter skin surfaces.

In other embodiments, the compositions are administered before the tissue desired to be protected manifests toxic effects of the systemically distributed anticancer therapeutic agent or metabolite thereof.

Often, this prophylactic or preventative administration of the one or more protectant agents, for example, uracil or a metabolite thereof is preferred. Such timing is particularly preferred in embodiments in which the one or more protectant agents, for example, uracil or a metabolite thereof is to be administered to the skin as the tissue desired to be protected— e.g. to prevent, ameliorate, delay, or treat hand-foot syndrome—because toxic side effects, once manifested in the skin, can increase its permeability to, or otherwise increase its absorption of, the protectant, potentially increasing the circulating concentration of the protectant agent, for example, uracil or a metabolite thereof.

The protectant agents may be used to also treat or counter side-effects from systemic anticancer therapeutic agents. Typically, the anticancer therapeutic agent or metabolite becomes systemically distributed upon or following systemic administration of the anticancer therapeutic agent, its metabolite, or a precursor thereof to the patient.

The anticancer therapeutic agent (or metabolite thereof) can be a chemical agent, a biological agent, a radiochemical agent or a radiobiological agent that has antineoplastic activity.

In some embodiments, the anticancer therapeutic agent, metabolite thereof, or precursor thereof is administered parenterally, such as by intravenous infusion, either continuous or bolus infusion, by intramuscular injection, by subcutaneous injection, or by intrathecal administration. In other embodiments, the anticancer therapeutic agent, metabolite thereof, or precursor thereof is administered orally. In yet other embodiments, the anticancer therapeutic agent, metabolite, or precursor is administered by transepithelial means, as by anal or vaginal suppository. In yet other embodiments, the anticancer therapeutic agent, metabolite, or precursor is implanted into the patient.

The systemically distributed anticancer therapeutic agent or metabolite can be an antimetabolite, such as a nucleotide, a nucleoside, or a derivative, analogue, or precursor thereof. For example, in certain embodiments, the systemically distributed anticancer therapeutic agent can be a purine antimetabolite such as mercaptopurine, azathioprine, thioguanine, or fludarabine. In other embodiments, the systemically distributed anticancer therapeutic agent can be a pyrimidine antimetabolite such as ara-C (cytarabine), gemcitabine, azacitidine, or a fluoropyrimidine, or a metabolite thereof.

In some of these embodiments, the systemically distributed anticancer therapeutic agent is a fluoropyrimidine.

The systemically distributed (typically, systemically administered) anticancer therapeutic agent can be associated with toxicity to an epithelium, such as an integumentary or mucosal epithelium. In certain embodiments, the toxicity is hand-foot syndrome. In these embodiments, the protectant is usefully administered topically to the palmar and/or plantar skin surface. In embodiments in which hand-foot syndrome is caused by systemic administration of a fluoropyrimidine, such as 5-FU or capecitabine, at least one of said at least one protectant agents is usefully uracil, usefully composited in a hydrophilic ointment for topical administration to the skin of the hands and feet.

In certain embodiments, the fluoropyrimidine is a parenterally administrable fluoropyrimidine, such as 5-FU, ftorafur, Carmofur, capecitabine, doxifluridine, UFT, S-1, or Emitefur. In other embodiments, the fluoropyrimidine is an orally administrable fluoropyrimidine, such as capecitabine, doxifluridine, or tegafur, alone or formulated in admixture with one or more inhibitors of dihydropyrimidine dehydrogenase (DPD). In certain embodiments, for example, the fluoropyrimidine (such as tegafur) can be administered in a composition that further comprises uracil and/or 5-chloro-2,4-dihydroxypyridine, and optionally oxonic acid. In another aspect, the invention provides pharmaceutical compositions for local application to a body tissue, the composition capable of establishing a local concentration of one or more protectant agents sufficient to protect the tissue from toxic effects of one or more systemically distributed anticancer therapeutic agents or metabolites thereof without abrogating the clinical efficacy of the systemically distributed anticancer therapeutic agent or metabolite. The composition comprises at least one protectant agent; and a pharmaceutically acceptable carrier suitable for local application.

In other embodiments, the anticancer therapeutic agent is an anthracycline, or precursor or metabolite thereof. In some of these embodiments, the anticancer therapeutic agent can be selected from the group consisting of doxorubicin, nonpegylated liposomal doxorubicin, pegylated liposomal doxorubicin, daunorubicin, liposomal daunorubicin, epirubicin, and idarubicin.

In other embodiments, the anticancer therapeutic agent can be a taxane, such as docetaxel or paclitaxel.

In embodiments of the methods of the present invention in which the tissue desired to be protected is rectal or colonic mucosa—typically, embodiments in which the systemically distributed anticancer therapeutic agent or precursor or metabolite thereof is administered to treat a condition other than colorectal carcinoma—the protectant compositions of the present invention can be formulated for administration by enema.

The compositions of the present invention may be packaged for single use or multiple uses, with multiple use packaging usefully designed to provide protectant composition sufficient for the duration of a concurrent course of systemic therapy with anticancer therapeutic agent.

For example, a uracil ointment useful in protecting palmar and plantar surfaces from the toxic effects of systemically distributed fluoropyrimidine or metabolite or prodrug thereof, may usefully be packaged in an amount sufficient for at least a 14-day or 21-day course.

The compositions of the present invention can also usefully be packaged in kits. The kits of the present invention can, for example, usefully comprise a protectant composition and an orally administrable anticancer therapeutic agent or precursor.

In some embodiments, the invention can comprise a protectant composition formulated for application to a skin surface, such as the palmar and/or plantar skin surface, and an orally administrable fluoropyrimidine, such as tegafar, Carmofur, capecitabine, doxifluridine, UFT, S-1, or Emitefur. In such embodiments, the kit can comprise a plurality of doses of orally administrable fluoropyrimidine, usefully a sufficient number of doses for a standard course of therapy, and a sufficient amount of protectant composition for administration during the course of oral chemotherapy. The plurality of doses of orally administrable fluoropyrimidine can be ganged together, for example in one or more blister packs.

6.2.2. General Treatment of Dermatoses

In other embodiments, the invention encompasses the surprising and unexpected effect of treating, managing, or preventing the onset or progression of various dermatoses. Dermatoses are known in the art to encompass disorders of the skin or dermis. By way of example, dermatoses may include atopic dermatitis, irritant contact dermatitis, radiation-induced dermatitis, dry skin dermatitis, papulopustular rashes, xerosis, pruritus, actinic keratosis, genital warts, superficial basal cell carcinoma, and combinations thereof.

In certain embodiments, the invention is directed to the surprising discovery that compositions including uracil or a metabolite thereof are useful in treating and/or preventing dermatoses. Dermatoses may include any disorder or disease of the skin.

In other embodiments, compositions including a therapeutically or prophylactically effective amount of uracil or a metabolite thereof may further be of use for treating, preventing, or managing Atopic Dermatitis (AD or eczema). In other embodiments, the compositions including uracil or a metabolite thereof are useful in treating, preventing, or managing dry, itchy, inflamed and scaly skin.

As used herein and unless otherwise indicated, the terms "therapeutically," "treatment," or "treating" refers to an amelioration of a disease or disorder associated with a dermatosis, or at least one discernible symptom thereof. In yet another embodiment, "treatment" or "treating" refers to inhibiting the progression of a disease or disorder associated with a dermatosis, either physically (e.g., stabilization of a discernible symptom), physiologically (e.g., stabilization of a physical parameter), or both. In yet another embodiment, "treatment" or "treating" refers to delaying the onset of a disease or disorder associated with a dermatosis.

As used herein and unless otherwise indicated, the phrase "therapeutically effective amount" of a Compound or Composition of the Invention or a pharmaceutically acceptable salt, solvate, metabolite, or prodrug thereof is measured by the therapeutic effectiveness of a compound of the invention, wherein at least one adverse effect of a disorder associated with dermatosis is ameliorated or alleviated. In one embodiment, the term "therapeutically effective amount" mean an amount of a drug or Compound of the Invention that is sufficient to provide the desired local or systemic effect and performance at a reasonable benefit/risk ratio attending any medical treatment. In one embodiment, the phrase "therapeutically effective amount" of a composition of the invention is measured by the therapeutic effectiveness of a compound of the invention to alleviate at least one symptom associated with dermatosis.

As used herein and unless otherwise indicated, the term "prophylactically effective" refers to an amount of a Compound or Composition of the Invention or a pharmaceutically acceptable salt, solvate, metabolite, or prodrug thereof causing a reduction of the risk of acquiring a given disease or disorder associated with dermatosis. Accordingly, the Compounds of the Invention may be used for the prevention of one disease or disorder and concurrently treating another (e.g., prevention of HFS, while treating pruritus). In certain embodiments, the compositions of the invention are administered to a patient, preferably a human, as a preventative measure against such diseases. As used herein, "prevention" or "preventing" refers to a reduction of the risk of acquiring a given disease or disorder associate with dermatosis.

In other embodiments, compositions including uracil or a metabolite thereof may further be used for treating or preventing radiation induced dermatitis. Patients undergoing radiation treatment often suffer radiation dermatitis, resulting in an interruption in their course of radiation. Radiation dermatitis manifests with dryness and itchiness in the affected area, pain or soreness of the skin, as well as breakdown and blistering.

In other embodiments, compositions including uracil or a metabolite thereof may further be used for treating patients with End-Stage Renal Disease who have pruritus associated with the disease. Persons undergoing hemodialysis treatment for end-stage renal disease may suffer from dry, cracked skin and moderate to severe pruritus. It is another facet of the invention that the protectant may alleviate the problems stimulated by recurrent hemodialysis.

In other embodiments, compositions including uracil or a metabolite thereof may further be used for treating premature infants often suffer skin disorders as they often lack a fully developed skin barrier, which puts them at higher risk for skin infections and divert a portion of their caloric intake to thermoregulation. The use of the present invention may provide treatment to alleviate the dermatological perils premature infants may face.

In some embodiments, compositions including uracil or a metabolite thereof may be applied topically to the skin to treat the skin suffering from a dermatosis. In other aspects, the compositions will be applied topically to prevent or protect the skin. By way of example, application of uracil or its metabolities or analogs thereof to the skin of a subject is useful for treating or protecting the skin from dermatoses.

In certain embodiments, compositions including uracil or a metabolite thereof are useful for patient suffering from a disease that can manifest with periodic outbreaks on the skin, such as genital warts. The compositions of the invention may be useful in preventing skin outbreaks. It will also be apparent to those skilled in the art that the compositions may be applied to prevent or treat acne outbreaks.

In particular embodiments, the compositions are combined with other topical agents to assist in treating or prevent a skin disease. By way of example, the uracil or metabolite thereof may be combined with anti-viral or anti-bacterial agents and applied together to the skin. Those skilled in the art will appreciate that restrictions on dosing, as well as other factors such as convenience, may provide for the topical application of other agents at separate times and/or intervals as the application of the compositions of the invention.

6.3 Kits

In yet a further aspect, the invention provides kits for oral delivery of an anticancer therapeutic agent or precursor ("prodrug") thereof with reduced toxicity to a desired tissue. The kit can comprise at least one dose of an orally administrable anticancer therapeutic agent or precursor thereof; an at least one dose of a locally administrable tissue protectant composition. In some embodiments, the orally administrable anticancer therapeutic agent or precursor is a fluoropyrimidine or fluoropyrimidine composition, such as ftorafur, Carmofur, capecitabine, doxifluridine, UFT, 8-1, or Emitefur.

In some of these embodiments, the protectant composition of the kit comprises uracil as the protectant; in certain of these embodiments, uracil is present in a weight/weight percentage of 1.0%.

Embodiments of the kits of the present invention can optionally, but usefully, comprise applicators, particularly in embodiments in which the protectant composition is intended for local administration to a tissue other than the skin surface.

Kits will typically also include instructions for administration of the protectant composition and, if the kit comprises an orally administrable anticancer therapeutic agent or precursor, instructions for oral administration of the oral agent. Kits will typically also include instructions for administration of the protectant composition and, if the kit comprises an orally administrable anticancer therapeutic agent or precursor, instructions for oral administration of the oral agent.

In some embodiments, the kits can include dressings, such as occlusive dressings, that facilitate the establishment of a sufficient local concentration of the protectant composition.

The invention additionally provides a metered-dose package for coadministration of a first and a second component of a therapeutic agent. The metered-dose package includes a first plurality of fluidly noncommunicating chambers, each of the chambers sealably containing an individual dose of the first component, and a second plurality of chambers, each of the chambers capable of reversibly receiving at least one dose of the second component.

The metered-dose package of the invention can include any of the kit embodiments described above and/or the safety or compliance systems described further below.

In one embodiment, the first and second component of a therapeutic agent includes, respectively, a protectant agent of the invention and an anticancer therapeutic of the invention. These therapeutics and protectant agents have been described above, any of which can be included in the metered-dose package of the invention. The first and second component of a metered-dose package of the invention is coadministered as described above. Therefore, all of the various combinations and permutations of a systemic anticancer therapeutic and a protectant agent above described or understood by one skilled in the art given the teachings and guidance provided herein are appropriate for inclusion in combination, for coadministration, in a metered-dose package of the invention.

A metered-dose package of the invention is particularly useful for associating the first and second components of a therapeutic agent where at least one of the components is to be administered in a predetermined dose—such as a maximal acceptable dose—or formulation, and the second component is to be administered in a variable, or individualized, dose, depending on patient factors with a dose prescribed by a physician.

In this regard, the metered-dose package of the invention includes a plurality first and second chambers. Such chambers can be, for example, the containers of the dispensers described further below. One plurality of chambers can be preloaded with a first component corresponding to the medicament having a predetermined, such as maximally acceptable, dose. The second plurality of chambers can be empty, or capable of reversibly receiving the medicament having a prescribed and variable dose. The second plurality of chambers can, for example, be filled by a pharmacist according to an individualized patient prescription.

In one specific example of the invention, the preloaded first component is a protectant agent of the invention, such as a uracil topical ointment. The empty chamber is designated for receiving a systemic anticancer therapeutic of the invention such as an orally administrable dose of capecitabine. The first plurality can be sealable chambers that are fluidly noncommunicating.

The above exemplary metered-dose package format is useful for efficient and effective dosing of both the systemic anticancer therapeutic and the protectant agent of the invention because it allows precise packaging of a predetermined dose, which dose may be a maximally acceptable dose, together with a variable dose.

This exemplary format also is beneficial for prescription accuracy and patient compliance of coadministered medicaments because it places the coadministered medicaments in association with each other in a concise and organized package easily understood by a patient. In this regard, a metered-dose package can be viewed as a precursor package for a safety or compliance system of the invention, later to be filled—or partially filled—with the prescribed anticancer therapeutic. Therefore, all of the attributes, characteristics, formats and permutations described below with reference to a safety or compliance system of the invention are equally applicable to a metered-dose package of the invention.

In further embodiments, a metered-dose package of the invention can include a first plurality of chambers that are capable of separately releasing their contained dose of first component. The wall bounding each of the first plurality of chambers can include an openable member. The openable member can be responsive to a variety forces including, for example, being openably responsive to the pressure within its respective chamber. In this latter embodiment, the wall member can open outwards in response to an increase in pressure within its respective chamber. In certain of these embodiments, for example, the wall member can open in response to pressures that exceed a threshold pressure, the threshold pressure being achievable by manual application of inward pressure to a site of the respective chamber's bounding wall positioned at a distance from the openable member. In various embodiments, the openable member can be pierceable.

In yet further embodiments, the first component can be flowable. Each dose of the flowable first component can be further constrained within a nonflowable dosage form, the constrained nonflowable dosage form being sealably contained with the chamber. For example, the flowable first component can be constrained within a breakable gel or gel capsule, each such gel or gel capsule being contained within one of the first plurality of chambers.

In some embodiments, the flowable component can be formulated for topical cutaneous administration. In other embodiments, which need not be mutually exclusive, the flowable component can be formulated for topical administration to oropharyngeal mucosae.

As described above and below, a metered-dose package of the invention can contain in each of the first plurality of chambers an identical dose of the first component. For example, the first component of the therapeutic agent can comprise uracil. The dosage of uracil can be any of the doses described above.

A metered-dose package of the invention also can be formatted to have each of the second plurality of chambers to be capable of reversibly receiving at least one solid dosage form of the second component. As with the first plurality of chambers, the second plurality of chambers also can include a bounding wall having an openable member. The openable member can be reversibly sealable. The second plurality of chambers also can be optionally filled with the second component. The second component can be any of the systemic anticancer therapeutics of the invention including, for example, capecitabine, Carmofur, tegafur, doxifluridine, S-1 and emitefur.

In one specific embodiment, the metered-dose package of the invention is capecitabine and the dose is either 150 mg or 500 mg. Accordingly, the plurality of doses of capecitabine includes a plurality of 150 mg and a plurality of 500 mg doses. In further specific embodiments, the plurality of first and/or second therapeutic agent component is sufficient, for example, for at least a one week course of therapy, al least a two week course of therapy, or at least a three week course of therapy.

Also provided is a safety or compliance system. The safety or compliance system includes at least one dispenser having a plurality of individual doses of a systemic anticancer therapeutic associated with a plurality of individual doses of a protectant agent formulated for nonsystematic delivery, each individual dose of the systemic anticancer therapeutic associated with each individual dose of the protectant agent enclosed in one or more individual compartments, the dispenser having suitable indicia marked in association with each individual compartment, thereby identifying each compartment with the day or time when the enclosed systemic anticancer therapeutic and protectant agent should be administered. The anticancer therapeutic can be capecitabine and the protectant agent can be a uracil topical ointment.

Patient compliance has been defined as "the extent to which an individual's behavior coincides with medical or health advice." (Remington's Pharmaceutical Sciences Chapter 103, Volume II, page 1796 (19th Edition (1995)). Conversely, non-compliance encompasses a variety of behaviors including drug underuse, which encompasses taking too low a dose or skipping a dose. Non-compliance also encompasses drug overuse such as taking too high a dose or taking a dose too frequently. Medication compliance is effected by the physician's and pharmacists relationship with the patient, and, in particular, how clearly the physician or pharmacist explains the treatment regimen to the patient. Non-compliance is generally higher in the elderly population than in other groups; for patients over the age of 65, about 20% of all non-elective hospital admissions are due to mismanagement of prescription medications. The increased incidence of non compliance in the elderly population may be due, for example, to declining mental function, increasing numbers of medications prescribed or an increase in side effects or drug interactions associated with multiple drug regimens (Murray et al., DICP 20:146 (1986)). Unfortunately, counseling, education and behavior modification techniques have achieved only limited success in boosting patient compliance. Pharmaceutical non-compliance is a particularly argent problem in the case of antineoplastic chemical compound therapies, a class of drug which can be fatal when ingested at excessive doses.

The present invention provides a safety or compliance system useful for home administration of a therapeutic agent such as the antimetabolites or anthracyclines described above in combination with one or more protectant agents. In particular, the invention provides a safety or compliance system that contains at least one dispenser including plurality of individual doses of a systemic anticancer therapeutic and a plurality of individual doses of a protectant agent formulated for nonsystemic delivery or administration, each individual dose of the systemic anticancer therapeutic is associated with each individual dose of the protectant agent and is enclosed in one or more individual compartments. Such a dispenser can have, for example, suitable indicia marked in association with each individual compartment, thereby identifying each compartment with the day or lime when the enclosed systemic anticancer therapeutic and/or protectant agent should be administered.

In a safety or compliance system of the invention, the dispenser can include, for example, at least two individual doses of systemic anticancer therapeutic and at least individual doses of protectant agent. A dispenser included in a safety or compliance system of the invention also can include, for example, a plurality of individual doses of systemic anticancer therapeutic in association with a comparable plurality of individual doses of protectant agent that corresponds to a prescribed treatment period.

It is understood that the safety or compliance systems of the invention can be useful for any patient prescribed a systemic anticancer therapeutic and protectant agent including, but not limited to, any outpatient-prescribed anticancer therapy and protectant agent that is associated with side effects due to the anticancer therapeutic. One skilled in the an understands that a safety or compliance system of the invention can be useful for patients suffering from any of a variety of disorders including, but not limited to, any of those described above such as breast cancer, colorectal cancer, head and neck cancer, and other neoplastic conditions.

A safety or compliance system of the invention contains at least one dispenser that includes a plurality of individual doses of systemic anticancer therapeutic in association with a plurality of individual doses of a protectant agent, each individual dose of systemic anticancer therapeutic and protectant agent are enclosed or positioned in one or more individual compartments. Such a safety or compliance system can have, for example, a single dispenser that includes a single daily dose, a weekly dose, a biweekly dose or a monthly dose of systemic anticancer therapeutic and protectant agent. Thus, a safety or compliance system of the invention is a pharmaceutical system that can contain any desired treatment regime of a systemic anticancer therapeutic and a protectant agent as one individual unit.

Systemic anticancer therapeutics can be prescribed in a variety of different treatment regimes. For example, capecitabine is typically prescribed as a daily individual dose for an interval of two weeks. The amount of capecitabine is determined by the surface area of the patient, and is typically administered orally using combinations of pills selected from 150 mg and 500 mg dosage strengths. A protectant agent such as uracil topical ointment can be administered in any of the dog dosages described above. A particularly useful ointment contains a concentration of about 0.1-1% uracil, with a dose in the range of about 0.4-2 g. As described above, protectant agents of the invention can be administered as a single dose once, twice or thrice daily, for example, for the duration of the anticancer treatment regiment. Applying a protectant agent in a nonsystemic delivery formulation such as a topical ointment beneficially raises the local concentration at the site of protection while the systemic concentration remains sufficiently low so as not to interfere with the systemic anticancer therapeutic effects.

The plurality of individual doses provided in a dispenser of the invention which corresponds to a daily, weekly, biweekly or monthly treatment regime of a systemic anticancer therapeutic included in a safety or compliance system of the invention is provided in an effective amount. Such an amount generally is the minimum dose necessary to achieve the desired reduction in severity of one or more symptoms of the condition to be treated over the course of the treatment, such as that amount roughly necessary to reduce the discomfort caused by the condition to tolerable levels or to result in a significant reduction in the discomfort caused by the condition. Such amounts generally are in the range of 0.1-5000 mg/day and can be, for example, in the range of 0.1-500 mg/day, 0.5-500 mg/day, 0.5-100 mg/day, 0.5-50 mg/day, 0.5-30 mg/day, 1-20 mg/day, 2.5-20 mg/day or 2.5-15 mg/day, with the actual amount to be prescribed and included in the safety or compliance system determined by a physician taking into account the relevant circumstances including the severity and type of condition to be treated, the age and weight of the patient, the patient's general physical condition, the cumulative dose, the characteristics of the active compounds and pharmaceutical formulation, and the route or routes of administration.

As used herein in reference to a systemic anticancer therapeutic or protectant agent of the invention, the term "daily," "weekly," "biweekly" or "monthly" dose means the total amount of systemic anticancer therapeutic and/or protectant agent prescribed or determined to be taken within the referenced treatment period (one day, seven days, 14 days or about 30 days). It is understood that individual doses can be prescribed to be administered, for example, as a single individual dose, or can be prescribed to be administered in two, three, or more individual doses, or can be prescribed to be administered in daily, twice daily or thrice daily individual doses to be taken every day of the week. Thus, where, within a biweekly treatment period (14 days), 2,100 mg capecitabine is prescribed to be administered as daily individual doses of equal amounts, the biweekly dose of capecitabine is 2,100 mg but the individual daily doses are 150 mg. Similarly, where, within a biweekly treatment period, 7,000 mg is prescribed to be administered as daily individual doses of equal amounts, the biweekly dose of capecitabine is 7,000 mg but the individual daily doses are 500 mg. It is understood that, where a dose for a particular treatment period is administered as a single dose, the dose for the referenced period will be the same as the individual dose, defined herein below.

Daily, weekly, biweekly or monthly doses of the systemic anticancer therapeutics of the invention are well known in the art and prescribed by a physician. Any of such doses can be included in the dispenser as, for example, a single individual dose, two or more individual doses, daily individual doses to be administered every day of the week, or twice daily individual doses to be administered every day of the week. In particular embodiments, any of such doses for a desired treatment period are included in the dispenser as daily individual doses to be administered every day of the week. In further embodiments, any of such doses are included in the dispenser as twice daily individual doses to be administered every day of the week, or as thrice daily individual doses to be administered every day of the week.

Daily, weekly, biweekly or monthly doses of a protectant agent formulated, for example, in a nonsystemic composition such as a topical ointment have been described above. Any of such doses can be associated with the chosen systemic anticancer therapeutic in a dispenser of the invention as, for example, a single individual dose, two or more individual doses, daily individual doses to be administered every day of the week, or twice daily individual doses to be administered every day of the week. In particular embodiments, any of such doses for a desired treatment period of protection are included in the dispenser as daily individual doses to be administered every day of the week. In further embodiments, any of such doses are included in the dispenser as twice daily individual doses to be administered every day of the week, or as thrice daily individual doses to be administered every day of the week. One skilled in the art understands that the dosages and treatment regimes exemplified herein for a systemic anticancer therapeutic associated with a protectant agent for dual administration and action are encompassed by the safety or compliance systems of the invention.

As used herein in reference to a systemic anticancer therapeutic or a protectant agent the term "individual dose" means the total amount of therapeutic and analog prescribed to be administered at a particular time, for example, on a particular day or particular hour of a particular day. Thus, an individual dose is defined by the time at which it is prescribed to be taken; such a dose can be provided, for example, as a single pill or multiple pills, which can be packaged together in the same compartment or packaged in two or more individual compartments, provided that the multiple pills are prescribed to be taken by the patient at the same time. In view of the above, it is understood that an individual dose can be composed of a single pill, tablet, capsule, spoonful, vial, ampule etc., or can be composed of multiple pills, tablets, capsules, spoonfuls, vials, ampules, etc., or a combination thereof. Two different individual doses are typically prescribed to be administered at two times separated by two or more hours such as, without limitation, four hours, eight hours, 12 hours, 24 hours or more. In specific embodiments, such an individual dose is administered one daily, twice daily or thrice daily.

The term "daily individual dose," as used herein in reference to a dose of a systemic anticancer therapeutic or a protectant agent, means an individual dose prescribed to be taken once a day. A daily individual dose is typically prescribed to be taken for several days in a row and can be prescribed to be taken at the same time of day.

As a non limiting example, an individual dose of a systemic anticancer therapeutic can be provided as a single tablet in a single compartment, or as multiple tablets packaged in a single or multiple individual compartments to be taken by the patient at the same time. As a further non limiting example, an individual dose of a systemic anticancer therapeutic and a protectant agent can be associated by packaging together in a single compartment or in two individual compartments, where the systemic anticancer therapeutic and protectant agent are prescribed to be administered together at the same time. As a further non limiting example, two or more individual doses of a systemic anticancer therapeutic can each be provided as a single tablet in two or more individual compartments to be administered, for example, two or more times daily, with protectant agent packaged together in the same compartment or associated with one or more daily doses of the systemic anticancer therapeutic. Generally, an individual dose of protectant agent of the invention will be administered with each individual dose of a systemic anticancer therapeutic and therefore have an association with each individual dose of the therapeutic.

As described above, the association between systemic anticancer therapeutic and protectant agent formulated for nonsystemic delivery can be in the same compartment or in different compartments. For example, pills, tablets, vials and the like of systemic anticancer therapeutic can be placed in a sealable container together with an individual dose of a protectant agent. The protectant agent can similarly be confined in a capsule, vial, gel cap and the like appropriate for the mode of nonsystemic administration. Alternatively, association of the individual doses for a systemic anticancer therapeutic and a protectant agent of the invention can be accomplished by, for example, structuring the dispenser of the safety or compliance system of the invention to contain pairs of containers in an organizational association that spatially associates the coadministered individual doses. Similarly, and as described further below, association of individual doses for a systemic anticancer therapeutic and a protectant agent of the invention also can be accomplished by, for example, inclusion of suitable indicia marked in association with each individual compartment that identifies each compartment with the day or time when the enclosed systemic anticancer therapeutic and protectant agent should be administered.

Although exemplified above with reference to individual doses deposited in single containers or in pairs of containers for association of a systemic anticancer therapeutic dose and a protectant agent dose, given the teachings and guidance provided herein, those skilled in the art will understand that such associations can be performed with three or more as well as larger pluralities of individual doses that are to be associated in the system of the invention for administration at the same time and date. Similarly, those skilled in the art also will understand that the associations described herein are only exemplary and that there exists a variety of other formats and permutations of compartmental structure, spatial at arrangements, indicia markings and all combinations thereof that can be routinely designed to achieve the same outcome and purpose of the various associations exemplified herein. Accordingly, the safety and compliance system of the invention provides the requisite association of an individual dose of a systemic anticancer therapeutic and of an individual dose of a protectant agent for a prescribed treatment regime and/or treatment period.

The term "dispenser," as used herein, means a structure that includes individual compartments, which are means for retaining and physically separating individual doses, or portions therefore, of a systemic anticancer therapeutic, a protectant agent or the combined individual doses for a systemic anticancer therapeutic and a protectant agent. It is understood that a dispenser is amenable to removal of an individual dose and that the individual compartments of a dispenser can open reversibly or irreversibly. In one embodiment, each individual compartment is located at a fixed position relative to the other individual compartments. A dispenser useful in the invention can optionally include, if desired, a visual or recordable means for indicating when individual compartments are opened.

In view of the definition of an individual dose, one skilled in the art understands that each individual compartment in a dispenser contains at most one individual dose of either a systemic anticancer therapeutic, a protectant agent or both a systemic anticancer therapeutic and a protectant agent but and never contains two or more individual doses of the same medicament together. In certain embodiments, an individual compartment can contain a portion of an individual dose as exemplified previously.

A variety of dispensers are useful in a safety or compliance system of the invention including, without limitation, a blister pack composed of for example, disposable cardboard or paper or a reusable plastic card; a surface with doses of medicament removably affixed thereto; a circular or substantially circular dispenser with compartments for every day of the month; a dispenser containing predetermined dose injection units; or a credit-card style medication package containing a month's worth of medication. Dispensers known in the art and suitable for use in the safety or compliance systems of the invention further include, but are not limited to, those described in U.S. Pat. No. 4,736,849; U.S. Pat. No. 4,889, 236; U.S. Pat. No. 5,265,728; U.S. Pat. No. 6,039,208; U.S. Pat. No. 6,138,866; U.S. Pat. No. 6,439,422; GB 2 237 204 A; publication 0 393 942 A1; and WO 01/68454 A2. Commercially available dispensers also are useful in the invention such as, without limitation, SlidePack7, E Ztear (PCI Services, Inc.; Cardinal Health), Pill Pak™, and DialPak7 tablet dispensers (Ortho Pharmaceutical Corporation; Raritan, N.J.). One skilled in the art understands that these and other disposable or refillable dispensers, including electronic dispensers and those with audio or visual cues, can be useful in the safety or compliance systems of the invention.

A safety or compliance system of the invention can include a plurality of dispensers. As non-limiting examples, a safety or compliance system can include one, two, three, four, five, six, seven, eight, nine, ten, eleven or twelve dispensers each containing a complete daily, weekly, biweekly or monthly dose of a systemic anticancer therapeutic associated with a like plurality of daily, weekly, biweekly or monthly doses of a protectant agent. Where multiple dispensers are packaged together in a safety or compliance system, the dispensers can be of the same or different types, and further can be of the same type containing identical or different individual doses of systemic anticancer therapeutic or protectant agent.

A blister pack is a dispenser which can be useful in the safety or compliance systems of the invention. As used herein, the term "blister pack" is a dispenser in which each compartment is an individual cavity having a rupturable backing. In one embodiment, the cavities or "pockets" are translucent. In a blister pack, individual doses of medication are dispensed by pushing the medication through the rupturable backing. In certain embodiments where the protectant agent of the invention is, for example, a topical ointment, the ointment can be directly loaded into the compartment extruded therefrom for administration. Alternatively, the protectant agent can be contained in a vial, gel cap or the like that can be removed from the compartment at the time of administration. The vial, gel cap or the like can be opened such as by tearing a perforated edge and the ointment can be extruded for topical or local application. The vial, gel cap or the like also can be removably attached to the inside of the compartment.

In one embodiment, a blister pack dispenser useful in the invention includes a first sheet having a plurality of apertures, each aperture defining an opening having an area large enough for the individual dose of systemic anticancer therapeutic or protectant agent to pass through; and a second sheet overlapping a portion of the first sheet, said second sheet forming a plurality of hollow cavities, said hollow cavities sealed with a rupturable backing to form a plurality of blister compartments arranged in a pattern on the sheet, with each rupturable backing arranged to overlap each aperture.

The first sheet generally is made of a moderately rigid material such as cardboard or coated cardboard, or plastic such as, without limitation, polyvinyl chloride of a thickness of about 0.5 mm to about 1 mm. The apertures can be of a variety of shapes, for example, circular, elliptical or of another shape appropriate to the egress of the anti folate therapeutic or folic acid analog. The second sheet is typically formed of a thin, flexible material such as clear polyvinyl chloride or other flexible material including, but not limited to, other translucent materials. The hollow cavities can be formed, for example, by thermal vacuum-drawing of the second sheet in accordance with standard practices in the packaging art. The rupturable backing can be formed, for example, of a thin layer of any of a variety of frangible materials such as metal foil. As one example, aluminum foil, of a thickness of between about 0.25 mm to 0.15 mm can be used as the rupturable backing. In one embodiment, a blister pack is of a size that can be conveniently accommodated in a shirt or other pocket. Such a blister pack can be, for example, of a size of 3 to 4 inches by 4 to 5 inches. A variety of blister packs are known in the art and have been described hereinabove.

As another non limiting example, a dispenser can be a DialPak7 tablet dispenser in which tablets are arrayed circularly and rotated one at a time to an aperture through which a selected tablet can be expelled from the package, with days of the week provided as indicia to guide the user to the appropriate tablet for the current day.

A dispenser useful in the invention optionally includes a visual or other recordable means for compliance monitoring, such dispensers are well known in the art and encompass, without limitation, U.S. Pat. No. 4,617,557; U.S. Pat. No. 5,289,157; U.S. Pat. No. 5,852,408; U.S. Pat. No. 6,401,991; WO 02/083057 A1; as well as the Medic™, ECM™, available from Information Mediary Corporation (Ontario, Canada). A recordable means for compliance monitoring also car be included in a safety or compliance system of the invention in a form separate from the dispenser. Non-limiting examples of separate recordable means can be found described in, for example, U.S. Pat. No. 6,075,755 or U.S. Pat. No. 4,837,719.

A dispenser useful in a safety or compliance system of the invention can be optionally marked with suitable indicia in association with each compartment. Such indicia can be, for example, the days of the week or the month or abbreviations therefore such as "M" "T" "W" "Th" "F" "S" "S" or, for example, "Day 1," "Day 2," etc. through "Day 7" or "Day 1," "Day 2," etc. through "Day 14" and/or "Day 31." Suitable indicia also can include, for example, the time of day such as, without limitation "morning" and "evening;" "breakfast" and "dinner;" "lunch" and "bedtime," "breakfast," "lunch," "dinner" and "bedtime;" or "A.M." and "P.M." In some cases, the indicia may apply to multiple compartments. As one example, a bracket or equivalent symbol can be used to indicate the same dose of systemic anticancer therapeutic and/or protectant agent included in multiple compartments. As a further example, in a calendar pack containing a month's worth of medication, the designation "Monday" placed above a column of four compartments can refer to each of the four compartments.

In particular embodiments, multiple dispensers are included in a safety or compliance system of the invention, with each dispenser containing, for example, medication exactly for a daily, weekly, biweekly or monthly treatment regime divided into individual doses and associated for coadministration of the systemic anticancer therapeutic and the protectant agent. In cases in which a safety or compliance system contains multiple dispensers, each separate dispenser can be optionally marked with "Week 1," "Week 2," "Week 3," "Week 4" etc. Alternatively, each dispenser can be optionally marked with "1", "2," "3," and "4" or "Dispenser 1," "Dispenser 2," "Dispenser 3," and "Dispenser 4" or other equivalent language. It is understood that multiple dispensers included together in a safety or compliance system of the invention may not be marked so as to be distinguishable from each other.

The suitable indicia marked in association with each compartment can include, if desired, the name of the systemic anticancer therapeutic or name of the protectant agent or appropriate abbreviation. As another option, the dose of one or both of the systemic anticancer therapeutic and protectant agents also can be marked on the dispenser in association with the appropriate compartment.

All of the elements of a safety or compliance system of the invention can be optionally packaged in an outer container made of any suitable material. Such an outer container can be constructed, for example, of any appropriate paper or plastic material, or a combination thereof. The outer container typically is of a size to accommodate standard pharmacy prescription labels and can have, without limitation, a rectangular or square shape.

It further is understood that a safety or compliance system of the invention, with or without an outer container, can be packaged in a child resistant manner or tamper-evident manner or both. Child resistant blister packages can incorporate, for example, at least one of the child-resistant features described in ASTM D 3475, or another feature which meets standard requirements for child resistance. Well known child-resistant blister cards included SlidePack7 and E-Ztear packages. Additional child resistant packaging, including child resistant blister packaging, also is well known in the art, as described, for example, in U.S. Pat. Nos. 3,503,493; 3,809, 220; 3,809,221; 3,924,746; 3,924,747; 4,011,949; 4,398,634; and 4,537,312. One skilled in the art understands that these and other child-resistant and tamper-evident dispensers and outer containers can be useful in a safety or compliance system of the invention.

A safety or compliance system of the invention optionally includes one or more reminder aids. Such a reminder aid can be, without limitation, one or any combination of reminder cards with information to remind the patient when to take a dose of medication; adhesive stickers with information to remind the patient when to take a dose of medication; or a visual or recordable means that is activated at the time an individual dose should be taken. It is understood that such recordable means encompass those to be set by the patient as well as those set, for example, by the manufacturer or pharmacist.

A safety or compliance system of the invention further optionally includes patient information provided separately from any outer container and the one or more dispensers. Such patient information can be provided, for example, as a paper insert or booklet and generally includes dosing information. The patient information provided cat further optionally include, without limitation, side effect information, patient incentive information or information on the disease being treated. The term "patient information," as used herein, means any information of interest to a patient being treated with a systemic anticancer therapeutic and a protectant agent. Such patient information includes, but is not limited to, any or all of the following: dosage information; importance of complying with dosage and administration instructions; side effect information, optionally including when during therapy side effects typically occur or how to manage side effects; anticipated benefits of therapy; and information regarding the disease or condition being treated. The patient information can additionally include, if desired, instructions regarding how and when to make up any missed doses as well as patient incentive information such as statements that encourage compliance by highlighting the benefits of proper administration. Patient information also can include, for example, warnings regarding possible drug interactions as well as conditions that may be inconsistent with the prescribed treatment or which may require a special dosage or special monitoring. The information is generally provided in a form which avoids complex and difficult medical terminology, using simple words appropriate to all educational levels.

The safety or compliance systems of the invention include both a systemic anticancer therapeutic and a protectant agent enclosed in a dispenser in association with each other. For convenience, the term "medicament" is used herein to mean either a systemic anticancer therapeutic or a protectant agent as described above and further below.

A safety or compliance system of the invention can optionally include any of a variety of drugs or other active compounds in addition to the systemic anticancer therapeutics and protectant agents of the invention. Such a drug or active compound can be for example, any drug or compound beneficial to an individual incurring cancer therapy and/or susceptible to side effects of such treatment.

A safety or compliance system of the invention can optionally include one or more placebos. A placebo lacks the anticancer therapeutic or the protectant agent or both and generally is any substance lacking significant pharmacological activity. In one embodiment, a safety or compliance system of the invention includes a placebo for every day on which no systemic anticancer therapeutic or protectant agent is prescribed.

As described previously, any of the systemic anticancer therapeutics and protectant agents of the invention can be included in a safety or compliance system of the invention in any of a variety of convenient or beneficial formulations. In one specific embodiment, the systemic anticancer therapeutic is formulated for oral administration as a pill and the protectant agent is formulated for nonsystemic delivery as a topical ointment. However, given the teachings and guidance provided herein, a systemic anticancer therapeutic and a protectant agent of the invention also can be formulated for other routes of administration, depending, for example, on the type and severity of condition to be treated, and the history, risk factors and symptoms of the subject. The formulations can be for the same or different routes of administration and associated in a dispenser of a safety or compliance system of the invention as exemplified previously. As described above, such formulations can be, for example, formulated for systemic administration for the anticancer therapeutic and for local or nonsystemic administration for the protectant agent. Formulations include, for example, compositions for oral administration or for administration by dermal patch; topical drops, creams, gels or ointments; or for parenteral administration; for subcutaneous, intramuscular, intravenous or other injection; and as extended release formulations. Acceptable dosage forms include, without limitation, tablets, pills, capsules, GelCaps (gelatin coated capsules) and other solid formulations, gels, creams, ointments, suppositories, powders, liquids, suspensions, emulsions, pre-filled syringes, aerosols and the like.

In some embodiments, the kits can include dressings, such as occlusive dressings, that facilitate the establishment of a sufficient local concentration of the protectant composition.

6.4. Combination Therapy

The compositions of the invention, which include a therapeutically or prophlactically effective amount of uracil or a metabolite thereof, can further include a therapeutically or prophlactically effective amount of a second active agent for treating, preventing or managing skin conditions.

In some aspects, the compositions further include a therapeutically or prophlactically effective amount of one or more antiviral compounds when the dermatosis is based on a viral infection, such as with herpes simplex-1 and -2, as well as fifth disease or other parvovirus B19 diseases. By way of example, the protectant agent may be used with antiviral agents such as abacavir, aciclovir, acyclovir, adefovir, amantadine, amprenavir, arbidol, atazanavir, brivudine, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, indinavir, inosine, integrase inhibitors, interferon type III, interferon type II, interferon type I, lamivudine, lopinavir, maraviroc, moroxydine, nelfinavir, nevirapine, nexavir, nucleoside analogues, oseltamivir, penciclovir, peramivir, pleconaril, podophyllotoxin, protease inhibitors, ribavirin, rimantadine, ritonavir, saquinavir, stavudine, tenofovir, tenofovir disoproxil, tipranavir, trifluridine, trizivir, tromantadine, valaciclovir, valganciclovir, vidarabine, viramidine, zalcitabine, zanamrivir, or zidovudine.

In other embodiments, the compositions further include a therapeutically or prophlactically effective amount of one or more anti-inflammatory agents, such as acetylsalicylic acid, NSAIDs, corticosteroids, anti-arthritics, gold or gold salts, DMARDs, methotrexate, cyclophosphamide, sulfasalazine, minocycline, azathipine cyclosporin, penicillamine, hydroxychloroquine, leflunomide, ibuprofen, naproxen, leukotriene inhibitors, COX-1 and/or COX-2 inhibitors, paracetamol, cortisone, corticosterone, arylalkanoic acids, 2-arylpropionic acids, N-arylanthranilic acids, pyrazolidine derivatives, oxicams, or sulfonanilides.

In other embodiments, the compositions further include a therapeutically or prophlactically effective amount of one or more anti-bacterial agents such as antispetics, antibiotics, alcohols, boric acid, azelaic acid, quaternary ammonium compounds, chlorohexidine gluconate, zinc, hydrogen peroxide, iodine, sodium hypochlorite, mercurochrome, octenidine dihydrochloride, phenol, sodium chloride, aminoglycosides, ansamycins, carbacephams, carbapenems, cephalosporins (first on, second, third, third, fourth, or fifth generation), macrolides, glycopeptides, monobactams, penicillins, polypeptides, quinolones, sulfonamides, chloramphenicol, tetracyclines, clindamycin, lincomycin, antifungals, metronidazole, rifampin, or isoniazid.

7. EXAMPLES

The following examples are offered by way of illustration only, and not by way of limitation.

7.1. Example 1

The theoretical systemic exposure to uracil from the topical application of a 1% w/w uracil ointment to the hands and feet can be crudely estimated as follows.

Application of 0.1 gm of a 1% (w/w) uracil ointment to the hands and feet four times a day represents an exposure of 4 8 mg of uracil/day. The topical absorption of agents through intact skin can be on the order of 1%, leading to a systemic absorption of 40-80 µg/day. This contrasts with exposure of about 1200 mg/day of uracil in UFT. Thus, the mean systemic uracil exposure with uracil ointment averages about 0.00005 (0.005%) that of UFT.

At the skin surface, however, and in the underlying skin, the concentration of uracil should be about 10 mg/ml. The average plasma 5-FU concentration is usefully estimated at 0.5 μg/ml. Thus, topical administration of uracil ointment theoretically establishes a local concentration of uracil that is approximately 2000-fold that of 5-FU at the skin, with a systemic dose only 0.005% that occasioned by oral administration of UFT.

7.2. Example 2

Figure 3D:
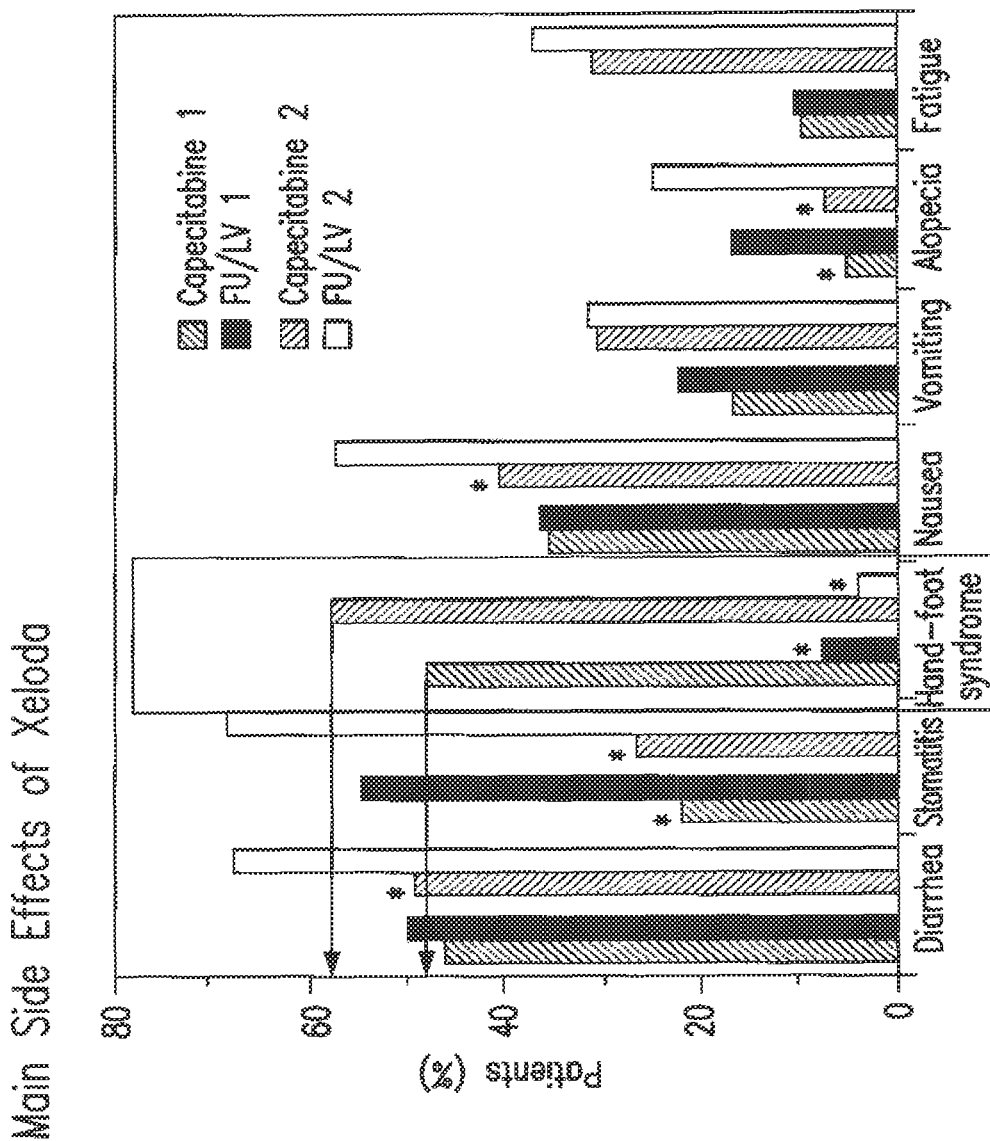
Figure 6:
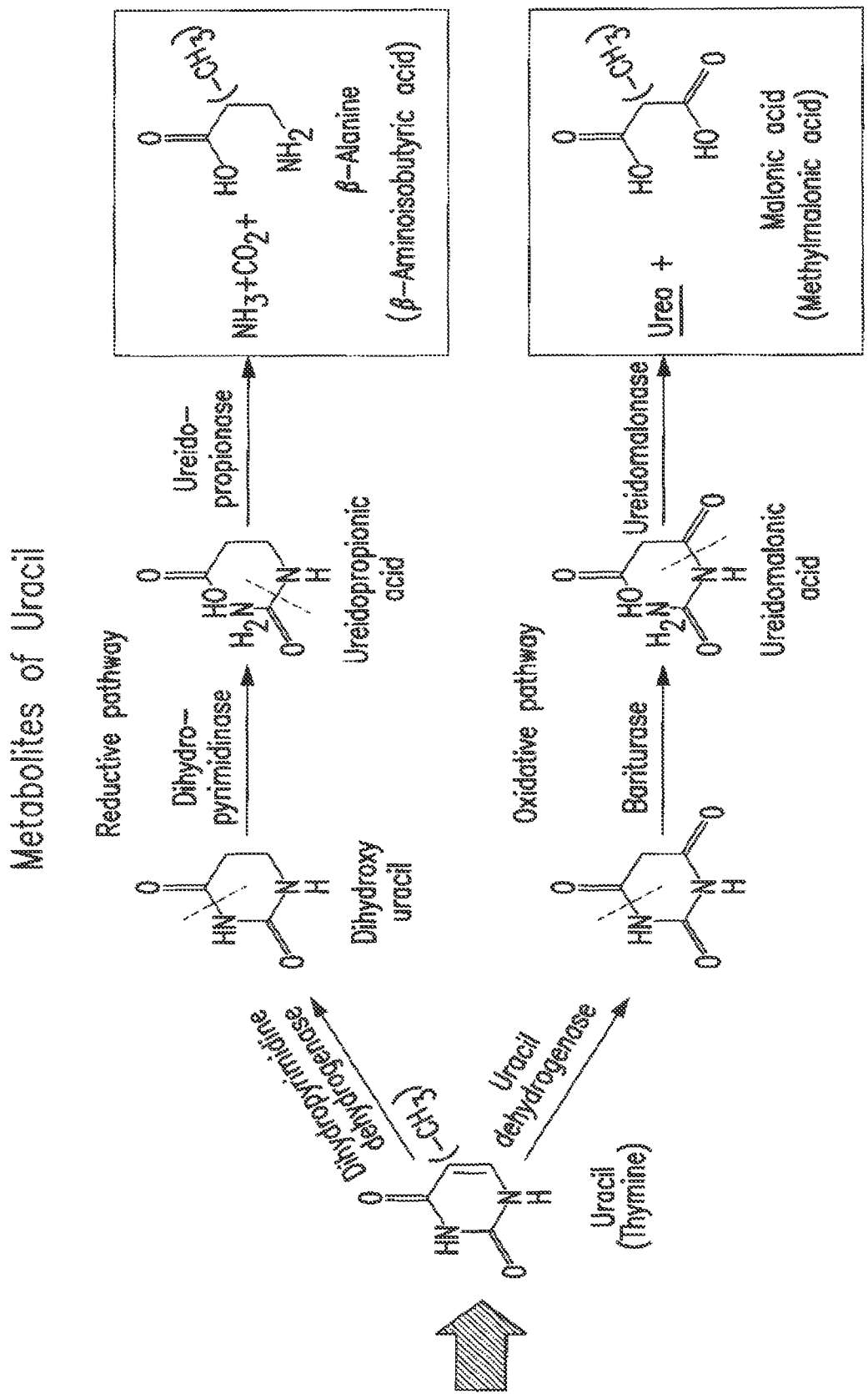
FIG. 6 illustrates the reductive and oxidative metabolic pathway of uracil (or thymine) metabolism to beta-alanine (or beta-aminobutyric acid) and malonic acid (methyl malonic acid).

A 48 year old female patient exhibited metastatic breast cancer. She had refused mastectomy and had previously failed adriamycin and cytoxan, weekly taxol, and weekly navelbine. She was then placed on Xeloda® together with 1% uracil ointment applied to the hands and feet. The 1% uracil ointment was used starting with cycle 5 of treatment with Xeloda®. FIGS. 3A, 3B and 3C illustrate the incidence of Hand and Foot syndrome in patients treated with Xeloda®.

Table 1 below summarizes results on this patient.

TABLE 1

| | Course q3wk | | | | | | | |
|---|---|---|---|---|---|---|---|---|
| | 1 | 2 | 3 | 4 | 5 | 6 | 7 | 8 |
| Xeloda dose 14/21 days | 1250 mg/m² bid × 14 | Same | D/C after 4 days | 1000 mg/m² bid × 14 | 1250 mg/m² bid × 14 | Same | Same | Same |
| Taxotere 75 mg/m² | + | + | + | + | + | + | + | + |
| Marker tumor size cm-prior to rx | 12 × 12 | 8 × 8 | 7 × 7 | 7 × 7 | 9 × 9 progression on lower dose Xeloda ® | 8.5 × 8.5 | 8 × 8 | 8.5 × 8.5 |
| 1% uracil ointment | 0 | 0 | 0 | 0 | + | + | + | + |
| Hand-foot syndrome | ND* | ND | ++++ | ++ | 0 | 0 | 0 | 0 |

*ND: Not described

The 1% uracil ointment allowed a re-escalation of the dose of Xeloda® with anti-tumor activity at the higher dose of Xeloda®. The 1% uracil ointment allowed a higher dose of Xeloda® to be administered with improved anti-cancer efficacy (compare columns 5 and 6). The 1% uracil ointment did not have any discernible toxicity.

7.3 Example 3

Another patient, a 68 year old white female diagnosed with metastatic colon cancer, was treated with Xeloda® and thalidomide. Hand-Foot Syndrome developed. Complete reversal of the syndrome occurred after topical treatment with a 1% uracil ointment. The efficacy of the Xeloda® and thalidomide treatment was unaffected by the concurrent use of 0.1 g 1% uracil ointment four times a day. There were no dose reductions of chemotherapy or treatment delays.

7.4. Example 4

A 60 year old white female with metastatic colon cancer was treated with 5-FU, Leucovorin®, and Oxaliplatin, a common regime of treatment for this form of cancer. The patient developed hand-foot syndrome.

Topical application of 0.1 g of 1% uracil ointment four time per day resulted in complete resolution of the syndrome. The anti-cancer treatment remained efficacious. No side-effects were noted as a result of the uracil ointment applications. There were no dose reductions of chemotherapy or treatment delays.

In total, 7 patients have been treated with 1% uracil ointment. In no case did hand-foot syndrome develop; there was no observable toxic reaction to the 1% uracil ointment.

7.5. Example 5

A patient with EGFR-expressing metastatic colorectal carcinoma undergoing systemic treatment with cetuximab (ERBITUX®) as single agent therapy develops dermatological toxicity, including skin drying and fissuring and acneform rash.

Cetuximab is a recombinant, human/mouse chimeric monoclonal antibody that binds specifically to the extracellular domain of the human epidermal growth factor receptor (EGFR), competitively inhibiting the binding of epidermal growth factor (EGF) and other ligands, such as transforming growth factor-.alpha.

The patient is treated topically at the site of skin toxicity with 10% EGF (recombinant) in ointment formulation two to four times a day, with reversal of skin toxicity manifestations, permitting the full and unattenuated course of cetuximab to be administered. Systemic absorption of EGF from the topical application of ointment has negligible effect on clinical efficacy of cetuximab therapy.

7.6. Example 6

A patient being treated with 5-FU by infusion according to the Roswell Park regimen develops diarrhea. The GI toxicity is presumed to result from the local activation of 5-FU by OPRT in the gut.

The patient is treated orally with a daily mixture of 10 mg of orotate together with 10 mg adenine in a slow release capsule formulation; diarrhea is reduced. Orotate, the natural substrate for OPRT, has about a 50-fold lower Km for OPRT than 5-FU at neutral pH. Adenine is included to balance purine (adenine) and pyrimidine (orotate) administration and synthesis. The change in systemic concentration of orotate and adenine is negligible.

7.7. Example 7

A patient is being treated with bevacizumab (AVASTIN™) in combination with intravenous 5-fluorouracil-based for metastatic carcinoma of the colon. Bevacizumab is a recombinant humanized monoclonal IgG1 antibody that binds to and inhibits the biologic activity of human vascular endothelial growth factor (VEGF).

The patient manifests skin toxicity.

A 1% w/v formulation of VEGF (recombinant) in an ointment formulation is applied to the affected skin areas two to four times per day, with resolution of the skin toxicity and negligible effect on the systemic concentration of VEGF.

7.8 Example 8

A patient being treated with CPT-11 (CAMPTOSAR®, Irinotecan) for therapy of metastatic colorectal carcinoma manifests serious diarrhea as a toxic side effect of chemotherapy. Irinotecan and its active metabolite SN-38 bind to the topoisomerase 1-DNA complex and prevent religation of single-strand breaks.

Aliquots of a mixture of plasmid DNA and topoisomerase I protein are sealed in dialysis membranes having MW cutoff sufficient to retain the protein/DNA complex and admit CPT-11. The patient ingests (without chewing) one such dialysis tubing twice per day, with significant reduction in diarrhea, due to partition of CPT- and/or SN38, the active metabolite, into the sealed dialysis membrane, reducing the level of CPT-11 to which the gastrointestinal mucosa is exposed. The reaction between SN38 and topoisomerase I and DNA requires only magnesium.

7.9. Example 9

The metabolism of uracil or analogs and derivative thereof to urea is useful for rehydrating the skin. It has previously been examined by Strahlenther (Onkol 179: 708-712, 2003) whether urea could effect radiation-induced skin toxicity. Briefly, Strahlenther observed 88 patients with carcinomas of the head and neck undergoing radiotherapy with curative intent (mean total dose 60 Gy, range: 50-74 Gy) were evaluated weekly for acute skin reactions according to the RTOG-CTC score. In 63 patients, moist skin care with a 3% urea lotion was performed. The control group consisted of 25 patients receiving conventional dry skin care. The incidence of grade I, II, and III reactions and the radiation dose at occurrence of a particular reaction were determined and statistically analyzed using the log-rank test. The dose-time relations of individual skin reactions are described.

At some point of time during radiotherapy, all patients suffered from acute skin reactions grade 1, >90% from grade II reactions. 50% of patients receiving moist skin care experienced grade I reactions at 26 Gy as compared to 22 Gy in control patients (p=0.03). Grade II reactions occurred at 51 Gy versus 34 Gy (p=0.006). Further, 22% of the patients treated with moist skin care suffered from acute skin toxicity grade III as compared to 56% of the controls (p=0.0007).

Moist skin care with 3% urea lotion delays the occurrence and reduces the grade of acute skin reactions in percutaneously irradiated patients with head and neck tumors.

7.10. Example 10

Hand foot syndrome (Palmar plantar crythrodysesthesia) is common side effect of capecitabine. FIG. 4 illustrates the frequency with which capecitabine treatment results in Hand and Foot syndrome, Grade II-III toxicity is seen in 10-50% of the patients and may lead to discomfort with activities of daily living. Interruption in the treatment and dose reductions are very frequent due to this toxicity. FIG. 5 shows the approach to coping with Hand and Foot syndromw through dose reduction. A study reported at the ASCO Annual Meeting in 2004 (Vol. 22, No. 14S at page 8105) analyzed the efficacy of local application of keratolytic agent urea (12.5%) (Cotoryl®) on capecitabine induced toxicity.

This study showed that patients on capecitabine were followed for signs of hand foot syndrome. Thirteen such episodes were recorded. Out of theses 4 episodes were of grade III and 9 of grade II toxicity. All had dry furrowed skin, rash, desquamation on the palms of the hands and soles of the feet. Patients with grade III toxicity had additionally painful erythema, discomfort with activities of daily living. All patients were asked to apply locally, twice a day, urea containing moisturizing ointment. The same preparation was used prophylactically in 7 cycles of capecitabine.

This application reportedly had a dramatic impact on dermatological complications within 2-3 days of initiation. The effect lasted till continuation of the application and lead to reduction in desquamation, pain, and comfort level of all the patients improved. Neurological symptoms reportedly improved as well. All patients were able to complete the chemotherapy cycle as per the schedule and without interruption or delays. Efficacy was seen in patients where it was used prophylactically. 5/7 did not develop cutaneous manifestation and two had grade I toxicity.

Urea containing preparation appears to be excellent choice for the prevention and treatment of capecitabine induced hand foot syndrome. This minimizes drag delays, schedule interruptions and maintains the dose density. Owing to reduced morbidity, the drug tolerance and acceptance is considerably improved.

7.11 Example 11

UFT® is a mixture of 5FU ad uracil in molar proportions of 1:4, which was chosen based on preclinical models that suggested maximal tumor selectivity with these relative concentrations. Uracil acts as a modulator on the catabolism of FU as it is a natural substrate for DPD, uracil will compete with 5FU. Furthermore, as its molar concentration is much higher than that of 5FU, little 5-FU is degraded by DPD, and thus, more is available to the anabolic route of activation.

Co-administration of 5FU and uracil may therefore produce a constant reserve of 5 FU and its active metabolites and to minimize production of inactive and potentially toxic metabolites.

7.12. Example 12

Ten patients have been treated from one to six months, with reports of complete efficacy in preventing Hand and Foot syndrome. Further, there have been no reports of toxicity. The projected systemic absorption of uracil from the claimed invention is described in Table 2. The calculations are based on topical application of 1 g of cream to the hands and 1 g to the feet twice a day, totaling 4 g. Uracil is at a concentration of 1% of the cream. A volume of distribution (Vd) of 50 L is assumed.

TABLE 2

| Percent Absorption | Total mg in body | Concentration (ng/mL) |
|---|---|---|
| 100 | 40 | 800 |
| 10 | 4 | 80 |
| 5 | 2 | 40 |
| 1 | 0.4 | 8 |

Given the chemistry of uracil, it is unlikely that more than 5% will be typically absorbed, indicating the concentration will be below 40 ng/mL. The normal level of uracil is reported to be 33.6+/−12 ng/mL (Ochoa et al. Annals of Oncology 10: 1313-1322, 2000). Accordingly, the present invention while efficacious for topical treatment, will not substantially increase the patient's systemic levels of uracil.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of treating hand and foot syndrome in a mammal by topically administering to a mammal in need thereof a therapeutically effective amount of a pharmaceutical composition comprising from about 0.01% (w/w) to about 3% (w/w) uracil and a pharmaceutically acceptable carrier.

2. The method of claim 1, wherein the composition comprises about 0.05% (w/w) of uracil.

3. The method of claim 1, wherein the composition comprises about 0.1% (w/w) of uracil.

4. The method of claim 1, wherein the composition comprises about 1% (w/w) of uracil.

5. The method of claim 1, wherein the composition is applied to an affected area of the skin.

6. The method of claim 1, wherein the administering maintains a moist wound and skin environment.

7. The method of claim 1, wherein the composition is administered at least once daily.

8. The method of claim 1, wherein the composition is administered at least twice daily.

9. The method of claim 1, wherein the mammal is a human.

* * * * *